(12) United States Patent
Rabin et al.

(10) Patent No.: US 12,383,686 B2
(45) Date of Patent: *Aug. 12, 2025

(54) PERCUTANEOUS DILATION TRACHEOSTOMY DEVICE AND METHOD OF USING

(71) Applicants: University of Maryland, Baltimore, Baltimore, MD (US); University of Maryland, College Park, College Park, MD (US)

(72) Inventors: Joseph Rabin, Silver Spring, MD (US); Conor Bloomer, Exeter, NJ (US); Paige Chan, Olney, MD (US); Scott Kivitz, Olney, MD (US); Peter Chen, Clarksburg, MD (US); Torrance Wang, Boyds, MD (US)

(73) Assignees: University of Maryland, Baltimore, MD (US); University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/438,696

(22) Filed: Feb. 12, 2024

(65) Prior Publication Data

US 2024/0181192 A1 Jun. 6, 2024

Related U.S. Application Data

(63) Continuation of application No. 18/055,586, filed on Nov. 15, 2022, now Pat. No. 11,896,763, which is a continuation of application No. 16/612,824, filed as application No. PCT/US2018/032014 on May 10, 2018, now Pat. No. 11,497,872.

(Continued)

(51) Int. Cl.
*A61M 16/04* (2006.01)
*A61M 16/08* (2006.01)

(52) U.S. Cl.
CPC .... *A61M 16/0472* (2013.01); *A61M 16/0465* (2013.01); *A61M 16/0816* (2013.01); *A61M 16/085* (2014.02)

(58) Field of Classification Search
CPC .. A61M 16/00; A61M 16/0003; A61M 16/04; A61M 16/0465; A61M 16/0472; A61M 16/08; A61M 16/085; A61M 16/0841; A61M 16/0816; A61M 29/00;
(Continued)

(56) References Cited

U.S. PATENT DOCUMENTS

| 4,520,810 A | 6/1985 | Weiss |
| 4,677,978 A | 7/1987 | Melker |

(Continued)

*Primary Examiner* — Colin W Stuart
(74) *Attorney, Agent, or Firm* — Riverside Law LLP

(57) ABSTRACT

The present invention provides an improved percutaneous dilation tracheostomy device. The device is configured to include all of the required components to perform a percutaneous tracheotomy. The device includes a retractable needle and an extendable j-wire rather than having separate components as in typical percutaneous tracheostomy devices. The device includes a dilator section to expand the diameter of a patient's stoma. The device is further configured to allow an operator to perform a bubble test to alert the user that the tube is in the trachea. In addition, the device is generally more compact than typical emergency tracheostomy devices.

18 Claims, 21 Drawing Sheets

Related U.S. Application Data

(60) Provisional application No. 62/608,232, filed on Dec. 20, 2017, provisional application No. 62/504,086, filed on May 10, 2017.

(58) Field of Classification Search
CPC ...... A61M 2205/073; A61M 2210/065; A61M 2210/1025; A61M 2210/1032
See application file for complete search history.

(56) References Cited

U.S. PATENT DOCUMENTS

| | | | |
|---|---|---|---|
| 5,217,005 A | 6/1993 | Weinstein | |
| 5,653,230 A | 8/1997 | Ciaglia | |
| 5,690,669 A | 11/1997 | Sauer | |
| 6,109,264 A | 8/2000 | Sauer | |
| 7,373,939 B1 | 5/2008 | Dubois | |
| 9,555,206 B1 | 1/2017 | Raimondi | |
| 11,497,872 B2 * | 11/2022 | Rabin | A61M 16/085 |
| 2003/0000526 A1 * | 1/2003 | Gobel | A61M 16/044 |
| | | | 128/204.18 |
| 2009/0199849 A1 | 8/2009 | Enk | |
| 2011/0290245 A1 | 12/2011 | Cuevas | |
| 2013/0025588 A1 * | 1/2013 | Bosel | A61M 16/0488 |
| | | | 128/200.26 |
| 2014/0000627 A1 | 1/2014 | Rosenbaum | |
| 2014/0128902 A1 | 5/2014 | Guerra | |
| 2016/0106940 A1 | 4/2016 | Bosel | |
| 2016/0361080 A1 | 12/2016 | Grace | |
| 2017/0136199 A1 * | 5/2017 | Lott | A61M 16/044 |

* cited by examiner

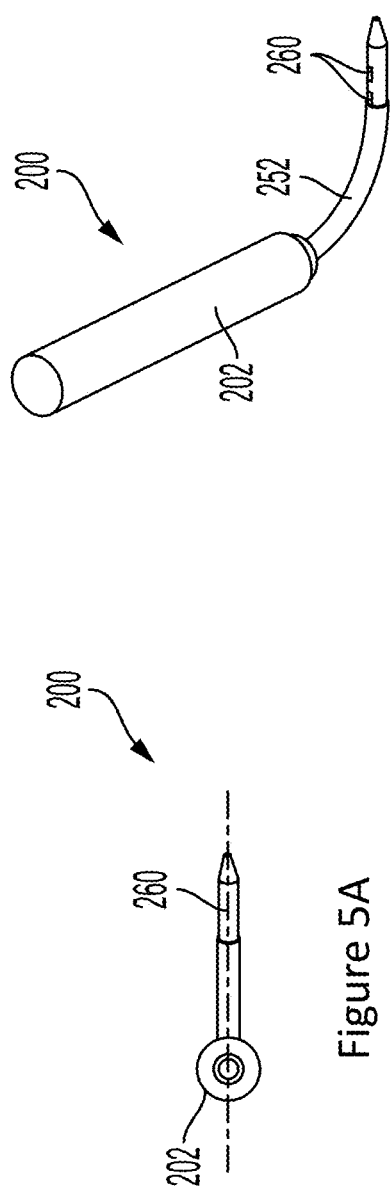
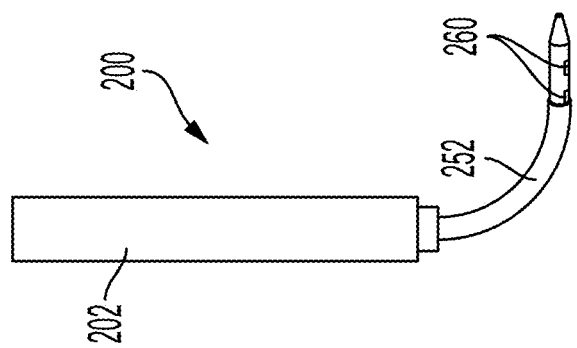
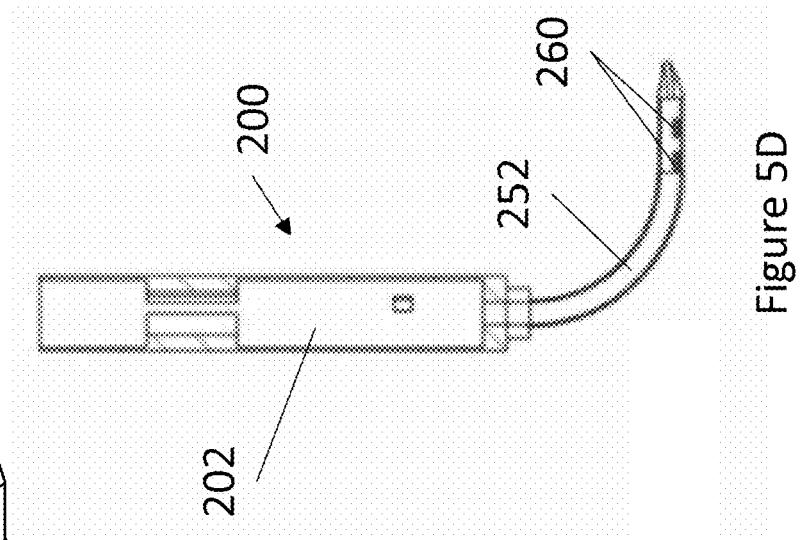
Figure 5A
Figure 5B
Figure 5C
Figure 5D

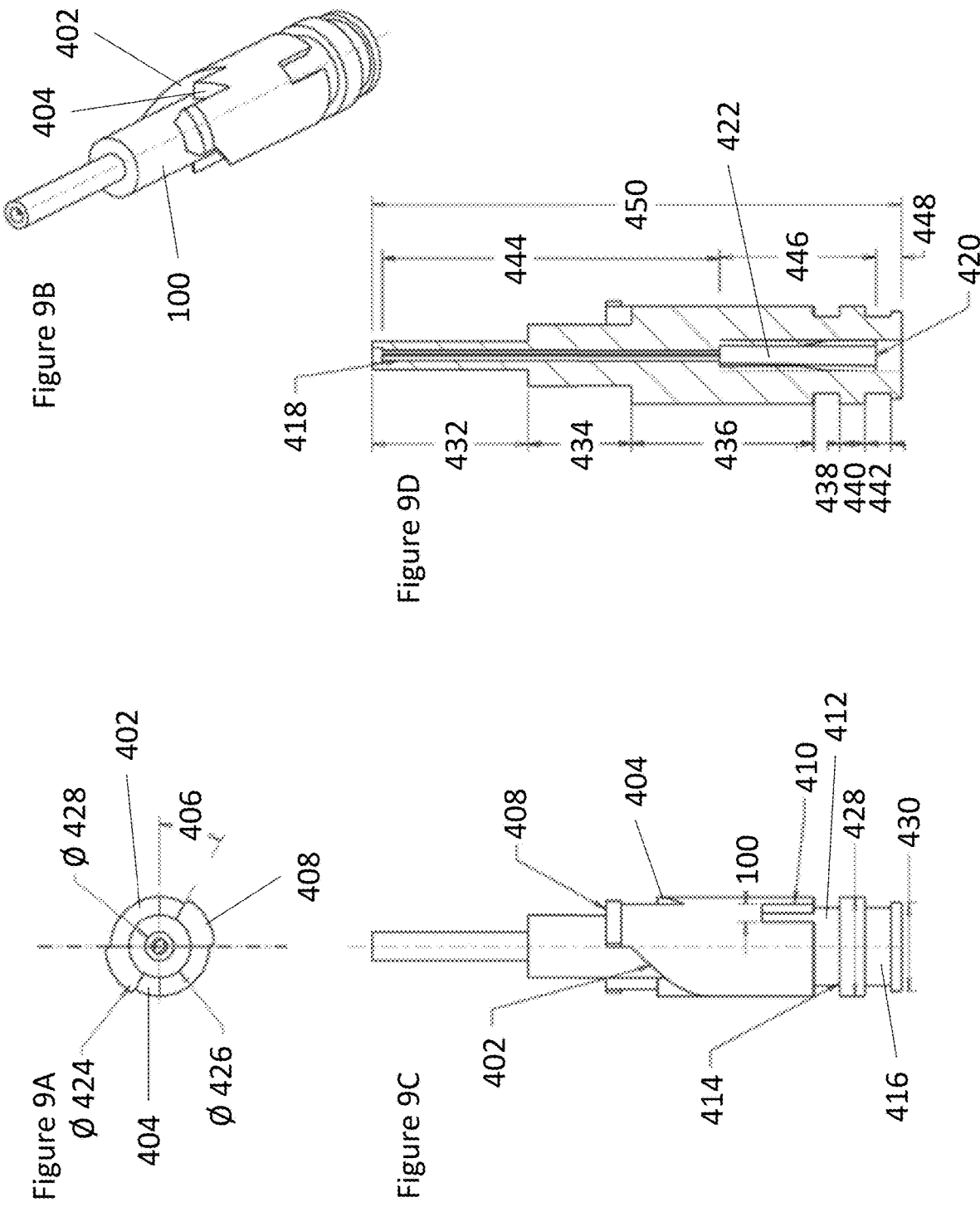

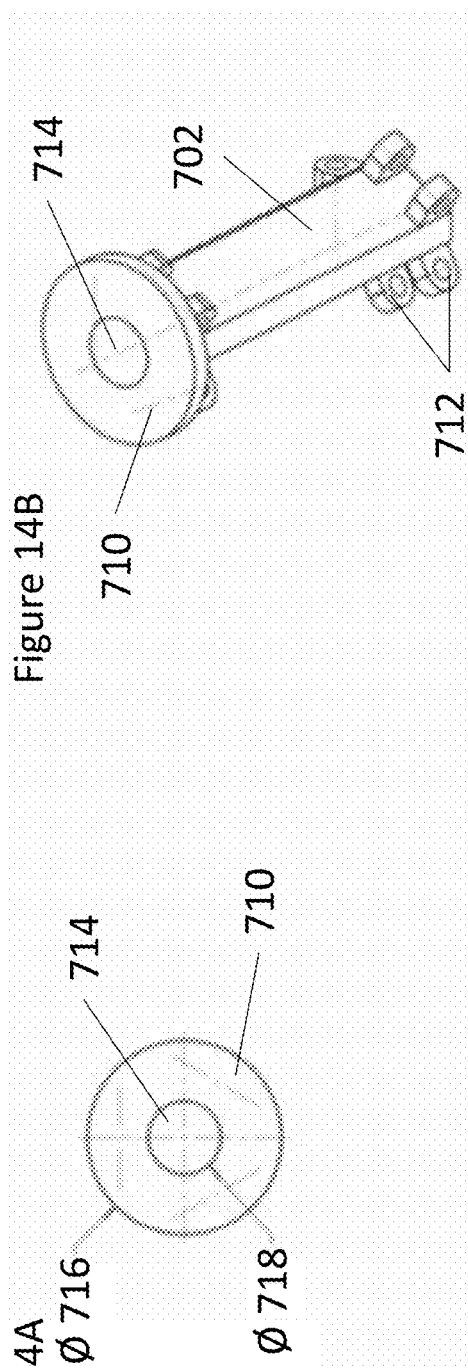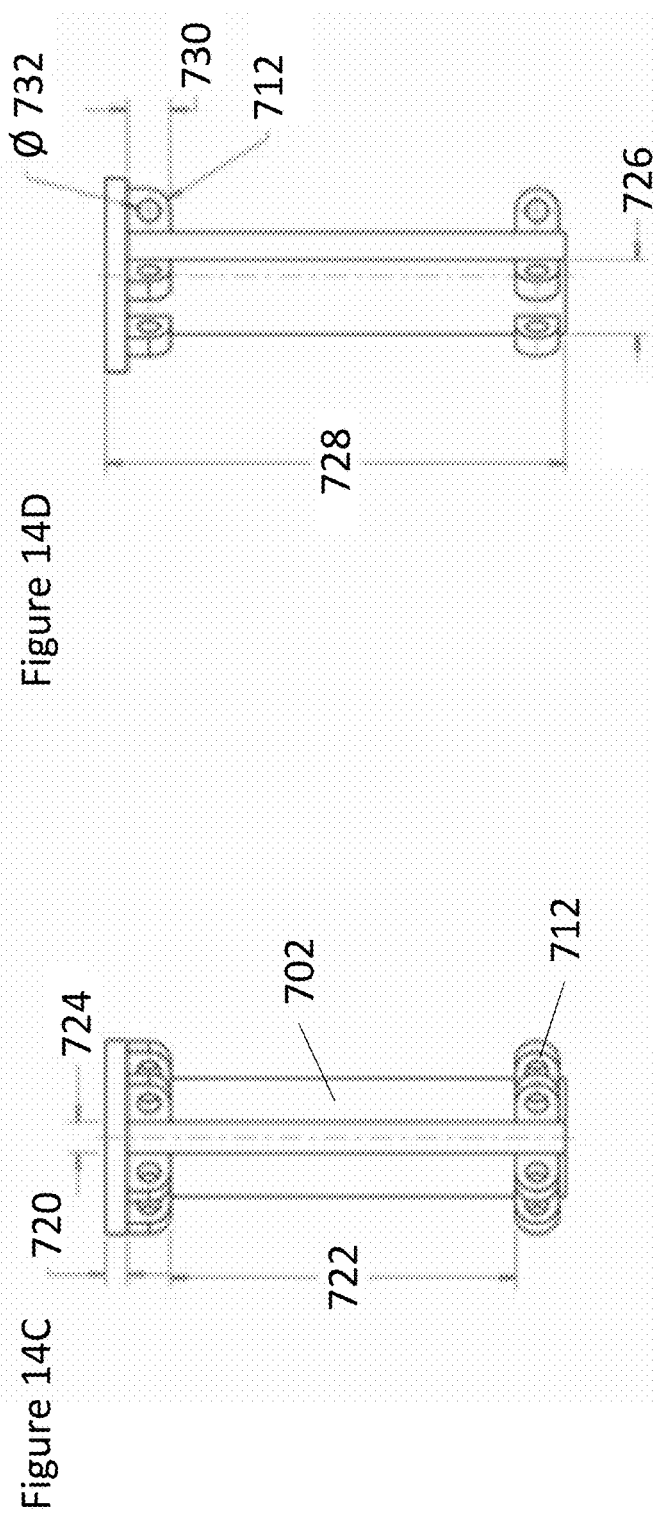

PERCUTANEOUS DILATION TRACHEOSTOMY DEVICE AND METHOD OF USING

CROSS-REFERENCE TO RELATED APPLICATIONS

This application is a continuation of U.S. patent application Ser. No. 18/055,586, filed on Nov. 15, 2022, now pending, which is a continuation of U.S. patent application Ser. No. 16/612,824, filed on Nov. 12, 2019, and which issued on Nov. 15, 2022 as U.S. Pat. No. 11,497,872, which is a U.S. national phase application filed under 35 U.S.C. § 371 claiming benefit to International Patent Application No. PCT/US2018/032014, filed May 10, 2018, which claims priority to U.S. Provisional Patent Application No. 62/504,086, filed May 10, 2017, and to U.S. Provisional Patent Application No. 62/608,232, filed Dec. 20, 2017, the contents of which are each incorporated by reference herein in their entirety.

BACKGROUND OF THE INVENTION

Tracheostomy tubes are placed to provide airflow and ventilation to the lungs and also protect a patient's airway. Tracheostomy tubes are often used to replace oral endotracheal tubes (i.e. intubation) and provide long-term airway access. The procedure can be done either surgically or percutaneously (percutaneous dilation tracheostomy, or PDT) in either an operating room or at the bedside in the intensive care unit (Epstein, 2005). A surgical airway can also be an emergent procedure for accessing the airway when traditional endotracheal intubation is not a possibility. Compared to oral endotracheal intubation, tracheostomy has many physiologic benefits. These include improved patient comfort, more efficient airway care, better oral care, and a more secure airway, which allows for safe patient transfer out of the acute-care ICU (Epstein, 2005).

The most common emergency surgical airway is a cricothyroidotomy to reduce the likelihood of anoxia and irreversible brain damage that may occur within three to five minutes of airway obstruction. A cricothyroidotomy is rapidly performed by placing an airway tube through the cricothyroid membrane to gain emergency access to the airway. Cricothyroidotomies are, however, associated with potential complications including bleeding, airway instability, and inadequate ventilation. Therefore, the airway tube is often quickly replaced with a standard tracheostomy in an operating room. In addition, the cricothyroid membrane is bounded by the thyroid cartilage and the cricoid cartilage, both of which are rigid members, making it difficult to dilate. As a result, this limits the size of the tube that can be placed (Epstein, 2005).

The average dimensions of the trachea are 2.3 cm in width and 1.8 cm from the posterior membrane to the anterior cartilage. In addition, the trachea is usually wider in men than in women (Epstein, 2005). In men, the tracheal diameter ranges from 1.3 cm to 2.5 cm and 1.3 cm to 2.7 cm in the coronal and sagittal planes respectively. In women, these are slightly less with diameters of 1.0 cm to 2.1 cm and 1.0 cm to 2.3 cm (Sasson, 2003). These dimensions vary with height and age. FIG. 1 shows the backbone of the neck region and the locations of where procedures would be performed.

Each year, over 100,000 tracheotomies are performed in the United States. The most common indications for a tracheostomy are (1) respiratory failure and need for a prolonged mechanical ventilation and (2) a neurological pathology or derangements that compromise a patient's ability to protect their airway. (Cheung & Napolitano, 2014). Such neurologic conditions include traumatic brain injury, stroke, spinal cord injury, anoxic brain injury, or other neurologic pathology that may compromise a patient's airway.

Traditionally, a surgical tracheotomy procedure is performed by a surgeon at the level of the proximal trachea usually between the second and fourth tracheal rings. The surgical procedure requires an incision and a careful subsequent dissection through the soft tissue and muscles in the anterior neck to access the trachea. One of various techniques is then used to create the tracheotomy, dilate this hole, and carefully insert the tracheostomy tube without compromising the patient's airway. This procedure can be time-consuming and is often associated with various risks including anoxia, infection, and bleeding.

A percutaneous tracheostomy device can simplify the procedure and reduce some of the risks by entering the trachea with minimal invasiveness. Other advantages include that it is relatively simple to perform, often involves a shorter procedure time, and may be performed bedside in an intensive care unit. The ability to perform a bedside procedure reduces the potential morbidity associated with transport of critically ill patients to the operating room. Several studies have also shown percutaneous tracheostomy to be more cost effective than surgical tracheostomy with similar or lower complication rates (Cothren, 2001).

The typical percutaneous dilatational tracheostomy (PDT) method was introduced in 1985 by Ciaglia (Byhahn, 2000). Since then, PDT has undergone a number of refinements and become just as safe and more cost-effective as surgical tracheostomies. Currently, many tracheostomies in intensive care medicine are done via PDT (Byhahn, 2000). When performing percutaneous dilatational tracheotomy, the tracheostomy (PDT) should be placed between the second and third tracheal rings (Epstein, 2005). PDT includes inserting multiple dilators of increasing size. On average, it takes more than six minutes to perform a PDT (Byhahn, 2000).

Precautions must be taken to avoid puncturing of the posterior wall of the trachea on initial needle cannulation. The recommended method is to insert the needle at 45 degrees to the long axis of the trachea pointing towards the thorax (Muhammad, 2000). In addition, rapid dilation of the tracheostomy may result in fractures to the tracheal rings (Byhahn, 2000).

The Ciaglia Blue Rhino® (CBR) is typical PDT device having a single special curved dilator. PDT with the CBR requires approximately 3 minutes to complete (Byhahn, 2000). The CBR kit still requires multiple components and procedural actions to dilate the hole in the trachea and insert the tracheostomy tube.

An alternative emergency tracheotomy technique is a PercuTwist tracheostomy set. The PercuTwist set uses a screw-like dilating device that lifts the anterior tracheal wall during dilation. A study 70 adult patients compared the PercuTwist to the CBR technique found that half of the patients had CBR tracheostomies and half had PercuTwist tracheostomies. Two cases of posterior tracheal wall injury were reported from the PercuTwist method. It is also important to note that cannula insertion was difficult in the PercuTwist cases while no such challenges were reported with the CBR. However, the study concluded that the differences were not significant and variations may be attributed to the relative inexperience the attending physicians had with the PercuTwist method. Neither the CBR nor PercuTwist are configured for use in emergency medicine, so patients must first be transported to the hospital before the procedure can be performed.

Ensuring the correct placement of a PDT device is key to minimizing complications. Correct placement can be especially challenging in patients with an abnormal tracheal anatomy. Patients with less than 1 cm between the cricoid ring and the upper end of the sternum are classified as having a short neck. In these patients, there is limited access to the upper tracheal rings and as result, it can make it difficult to accurately place the tracheostomy. Lastly, long shank adjustable tracheostomy tubes may need to be used for these patients because conventional tubes are too short (Muhammad, 2000).

Another example of altered tracheal anatomy is a deep lying trachea. Performing PDT on these patients can be hazardous as control of hemorrhage from inadvertent puncture of a vessel deep in the neck would be difficult. In addition, the trachea in these patients may also be deviated from the midline, therefore making safe cannulation of the trachea difficult. Lastly, anatomical landmarks may be lost, making identification of the upper tracheal rings and accurate cannulation difficult. For these patients, it is recommended to perform PDT in the operating room under general anesthesia, full monitoring, fiber-optic endoscopic control, and close surgical support (Mohammad, 2000).

Therefore, there is a need in the art for improved percutaneous tracheostomy devices. The present invention addresses this need.

SUMMARY OF THE INVENTION

In one aspect, the present invention provides a percutaneous dilation tracheostomy device comprising: a hollow casing having an elongate cylindrical proximal section and a curved tubular distal section; a depressible cylindrical plunger having a proximal end and a distal end positioned within the proximal section of the casing, the plunger having a lumen extending throughout; a rotatable cam positioned within the proximal section of the casing distal to the plunger, the cam having a lumen extending throughout and housing a j-wire catch and a needle catch; an elongate flexible plunger connector positioned within the proximal section of the casing distal to the cam and extending into the distal section of the casing, the plunger connector having a lumen extending throughout; two or more hinged wall members positioned on the distal section of the casing, the wall members being mechanically linked to a distal end of the plunger connector; a flexible j-wire connected to the j-wire catch at a proximal end and extendable out of the distal end of the plunger connector at a distal end; and a flexible needle connected to the needle catch at a proximal end and extendable out of the distal end of the plunger connector at a distal end, the needle having a lumen extending throughout.

In one embodiment, the wall members are expandable between a retracted configuration that positions each wall member flush against the distal section of the casing and an extended configuration that positions each wall member equidistantly away from the distal section of the casing. In one embodiment, the mechanical link between the plunger connector and the wall members comprises a dilator column hingedly connected to six struts, each wall member being hingedly connected to two struts. In one embodiment, the distal section of the casing comprises six openings through which each of the six struts extend from the hollow interior to the exterior of the casing. In one embodiment, the plunger is depressible to advance the plunger connector and the dilator column in a distal direction to slide each of the six struts out of each of the six openings and radially extend each wall member from a retracted position configuration to an expanded configuration.

In one embodiment, the plunger is depressible to rotate the cam at least two steps. In one embodiment, the first rotation step is configured to extend the j-wire stop and the j-wire and to retract the needle stop and the needle. In one embodiment, the second rotation step is configured to expand the wall members.

In one embodiment, the plunger is mechanically linked to a dilator column hingedly connected to six struts, each wall member being hingedly connected to two struts, in the absence of a cam, a needle catch, a j-wire catch, and a plunger connector, such that the plunger is depressible to radially extend the wall members.

In one embodiment, the lumen of the plunger, the cam, the plunger connector, and the needle are fluidly connected. In one embodiment, the proximal section of the casing further comprises at least one side port fluidly connected to an aperture positioned at the distal end of the casing. In one embodiment, the at least one side port is configured to attach to a source of ventilation gas or an end tidal CO2 detector. In one embodiment, the at least one side port is configured to accept the introduction of a j-wire.

In one embodiment, the distal section of the casing has an outer diameter between about 5 mm and 25 mm. In one embodiment, the distal section of the casing is dimensioned to fit within the lumen of a tracheostomy tube. In one embodiment, the wall members are configured to dilate the diameter of the distal section of the casing by between about 3 mm and 15 mm. In one embodiment, the wall members are configured to support an applied pressure of at least 15 MPa when expanded.

In another aspect, the present invention provides a method of inserting a tracheostomy tube into the trachea of a subject in need thereof, comprising the steps of: providing a percutaneous dilation tracheostomy device of claim 1, the device having a tracheostomy tube fitted over the distal section of the casing; forming an incision on the anterior neck of the subject while palpating for cartilage of the trachea; inserting the needle of the device between the cartilage of the trachea; depressing the plunger to extend the j-wire and to retract the needle; advancing the device into the trachea such that the wall members are positioned adjacent to the cartilage of the trachea; depressing the plunger to expand the wall members; sliding the tracheostomy tube off of the device and into the trachea; and removing the device from the trachea.

In one embodiment, the step of depressing the plunger to extend the j-wire and to retract the needle is preceded by a step of inserting a syringe loaded with a fluid into the lumen of the plunger and withdrawing the syringe to perform a bubble test. In one embodiment, the device is provided with a source of ventilation gas attached to a side port on the proximal section of the casing. In one embodiment, the device is provided with an end tidal CO2 detector attached to a side port on the proximal section of the casing.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 4A is a side view of the device with casing removed. FIG. 4B is a perspective view of the device with casing removed. FIG. 4C is a cross-sectional side view of the device within a casing.

FIG. 5A through FIG. 5D depict the casing of an exemplary percutaneous dilation tracheostomy device. FIG. 5A is a top view. FIG. 5B is a perspective view. FIG. 5C is a side view. FIG. 5D is a cross-sectional side view.

FIG. 6A is a top view. FIG. 6B is a side view. FIG. 6C is a perspective view.

FIG. 7A is a top view. FIG. 7B is a perspective view. FIG. 7C is a side view. FIG. 7D is a cross-sectional side view.

FIG. 8A is a top view. FIG. 8B is a perspective view. FIG. 8C is a side view. FIG. 8D is a cross-sectional side view.

FIG. 9A through FIG. 9D depict the cam of an exemplary percutaneous dilation tracheostomy device. FIG. 9A is a top view. FIG. 9B is a perspective view. FIG. 9C is a side view. FIG. 9D is a cross-sectional side view.

FIG. 10A is a top view of the j-wire catch. FIG. 10B is a perspective view of the j-wire catch. FIG. 10C is a top view of the j-wire rotational hold. FIG. 10D is a perspective view of the j-wire rotational hold. FIG. 10E is a top view of the needle catch. FIG. 10F is a perspective view of the needle catch.

FIG. 12A is a top view. FIG. 12B is a perspective view. FIG. 12C is a side view. FIG. 12D is a cross-sectional side view.

FIG. 13A is a perspective view. FIG. 13B is a side view.

FIG. 14A through FIG. 14D depict the column of the dilator of an exemplary percutaneous dilation tracheostomy device. FIG. 14A is a top view. FIG. 14B is a perspective view. FIG. 14C is a side view. FIG. 14D is a cross-sectional side view.

FIG. 15A is a top view. FIG. 15B is a perspective view. FIG. 15C is a side view.

FIG. 16A is a top view.

FIG. 16B is a perspective view. FIG. 16C is a side view. FIG. 16D is a cross-sectional side view.

FIG. 20A depicts the deformation of the wall members under an external pressure.

DETAILED DESCRIPTION

Figure 1B:
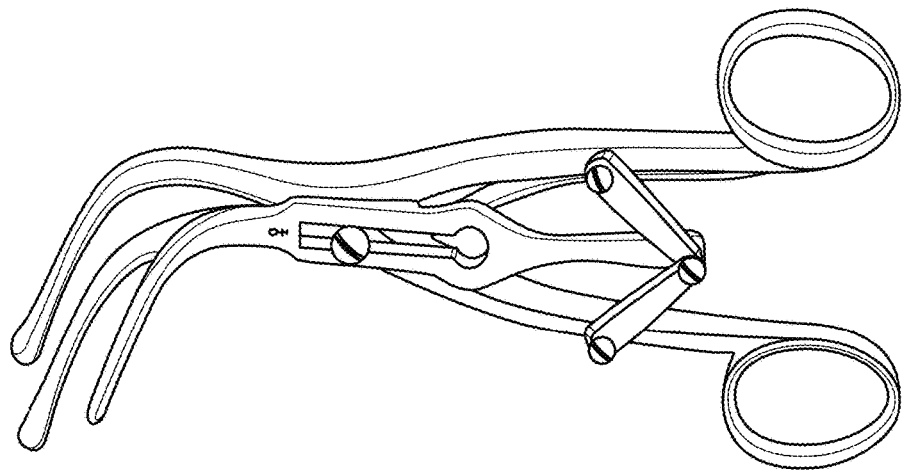
FIG. 1B is an illustration of a typical Laborde dilator.
Figure 1A:
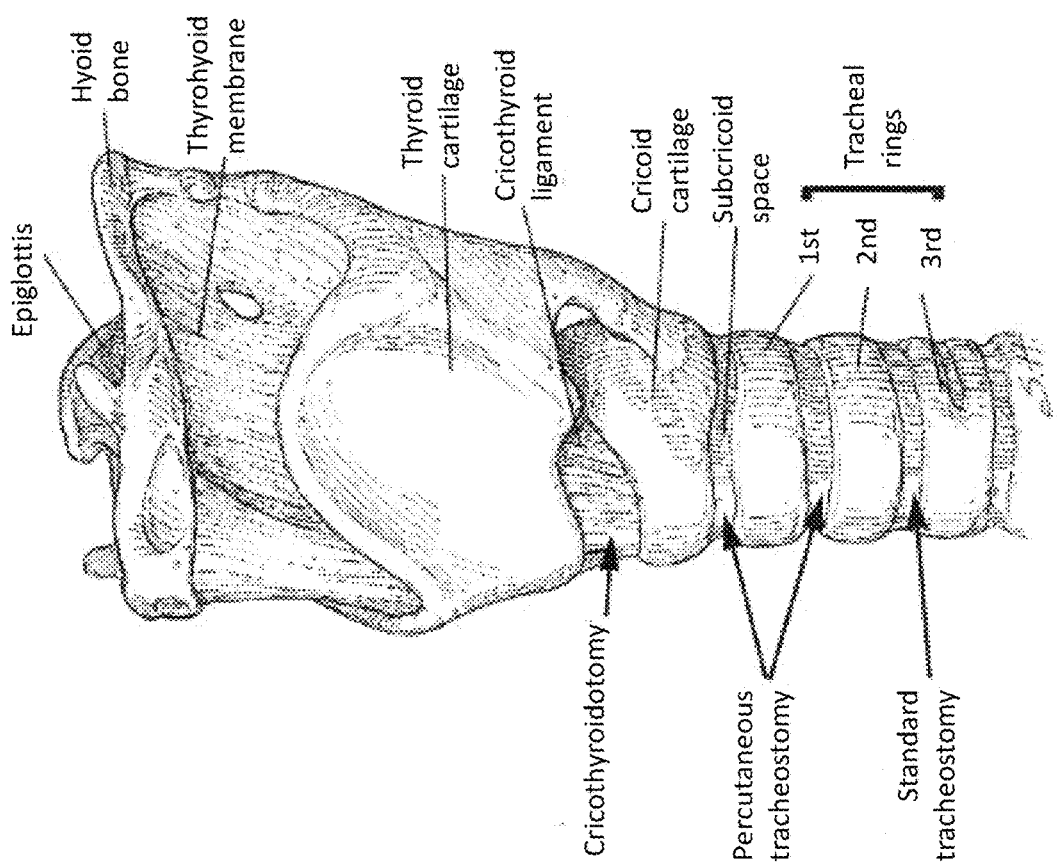
FIG. 1A is an illustration of a patient's neck region and the points of entry for a typical tracheotomy.

The present invention provides improved percutaneous dilation tracheostomy devices. The devices increase the safety, delivery, and efficiency of a percutaneous tracheotomy for traditional and emergent cases. The improved percutaneous dilation tracheostomy devices have a reduced parts count compared to typical percutaneous tracheostomy kits. The device according to a current embodiment includes a radially expanding region or dilation walls to dilate a patient's tracheal orifice. The device decreases the required number of steps or maneuvers to insert a tracheostomy tube, thus reducing the time required to safely perform a percutaneous tracheotomy. The device can also be used in emergency airway procedures.

The improved percutaneous dilation tracheostomy device is configured to provide feedback to the operator during while dilating the trachea during the procedure. The device includes a plunger that operates through mechanical pressure provided by an operator, allowing the operator to dilate to the desired size within a specified size range at a controlled rate of expansion. The operator depresses the plunger to force the dilator radially outward so the dilation walls press against a patient's cartilaginous tracheal rings to dilate the patient's stoma. In one embodiment, the plunger mechanism squeezes a compressible material outwards to dilate the opening. The plunger also includes a locking mechanism configured for the operator to control expansion of the opening. Thus, the operator dilates the trachea by expanding the dilation walls to a desired size.

The device is configured to include all of the required components to perform a percutaneous tracheotomy. The devices include a retractable needle, rather than having a separate component as in typical percutaneous tracheostomy devices. The retractable needle is attached to the tip of the device and the operator creates the initial puncture in the patient's trachea and retracts the needle into the device after entry into the patient's tracheal lumen is confirmed by a bubble test. A guide wire is then extended which helps maintain airway access throughout the remaining procedure. The device gradually becomes wider along its length to help safely initiate the dilation process and further secure the airway access. Finally, a dilation mechanism is configured to control the complete stoma dilation. The device is further configured to introduce the final tracheostomy tube so as to remove the device while the final tracheostomy tube remains in the patient.

General aspects of the design include ease of use, cost, and safety. The device is formed of materials that are approved for medical use. The device is generally ergonomic, such that it is comfortable for the operator to use. In addition, the device is configured to be low-cost such that it can be disposable. The devices are further configured to reduce the number of steps or maneuvers to perform a percutaneous tracheotomy by consolidating various required components into a single device. The device can also be used in patients requiring an elective tracheostomy.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Percutaneous Dilation Tracheostomy Device

The present invention provides devices configured to increase the delivery, efficiency, and reliability of a percutaneous tracheotomy both emergently and electively. The improved percutaneous dilation tracheostomy devices have reduced parts counts compared to typical tracheostomy components. The devices include a radially expanding dilator region. Thus, the devices can be configured for an operator to perform a tracheostomy in conjunction with typical tracheostomy components, such as a scalpel to make an initial incision, a syringe to perform a bubble test, and a tracheostomy tube.

Figure 2:
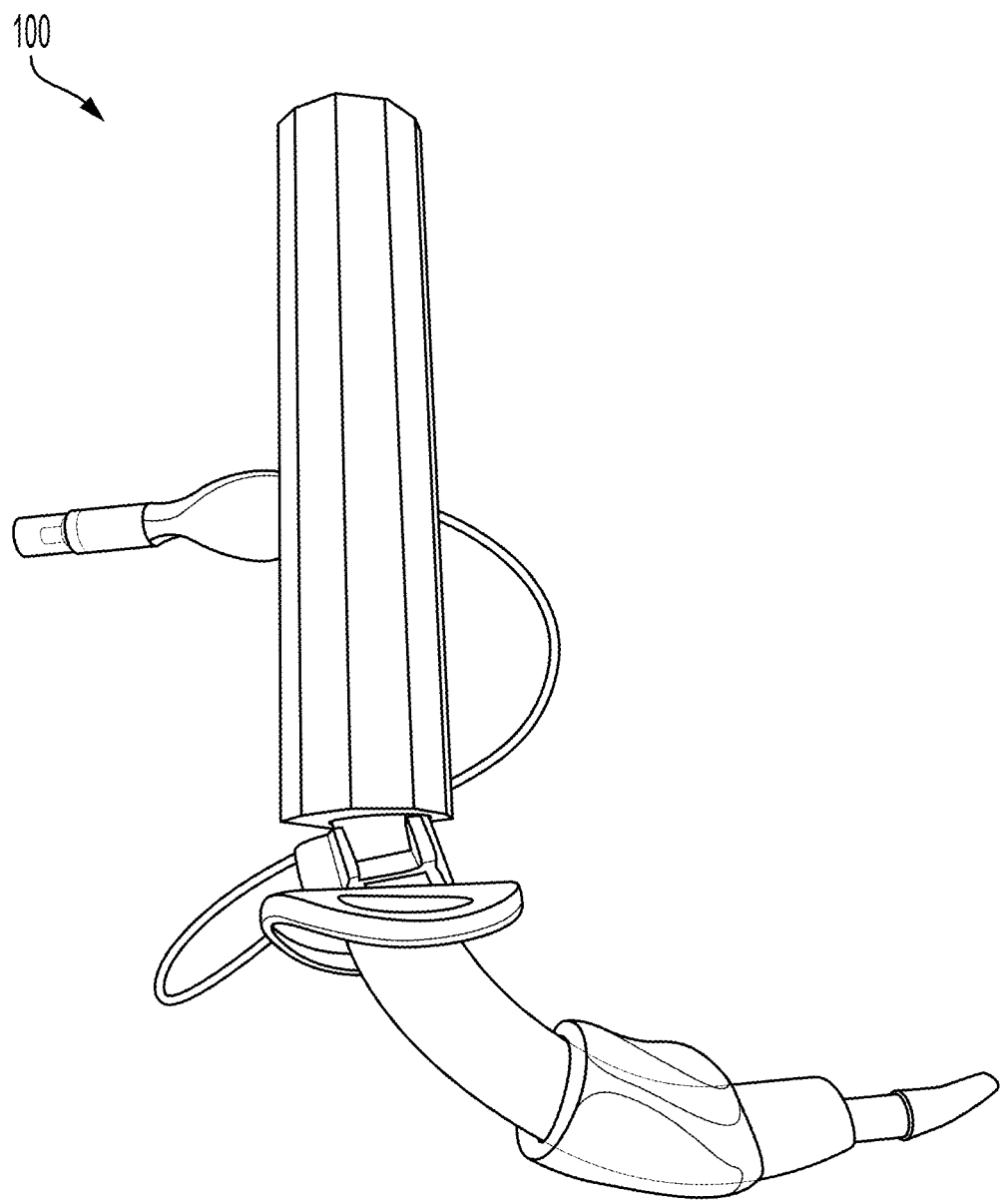
FIG. 2 is a photograph of an exemplary percutaneous dilation tracheostomy device with a preloaded tracheostomy tube.
Figure 3:
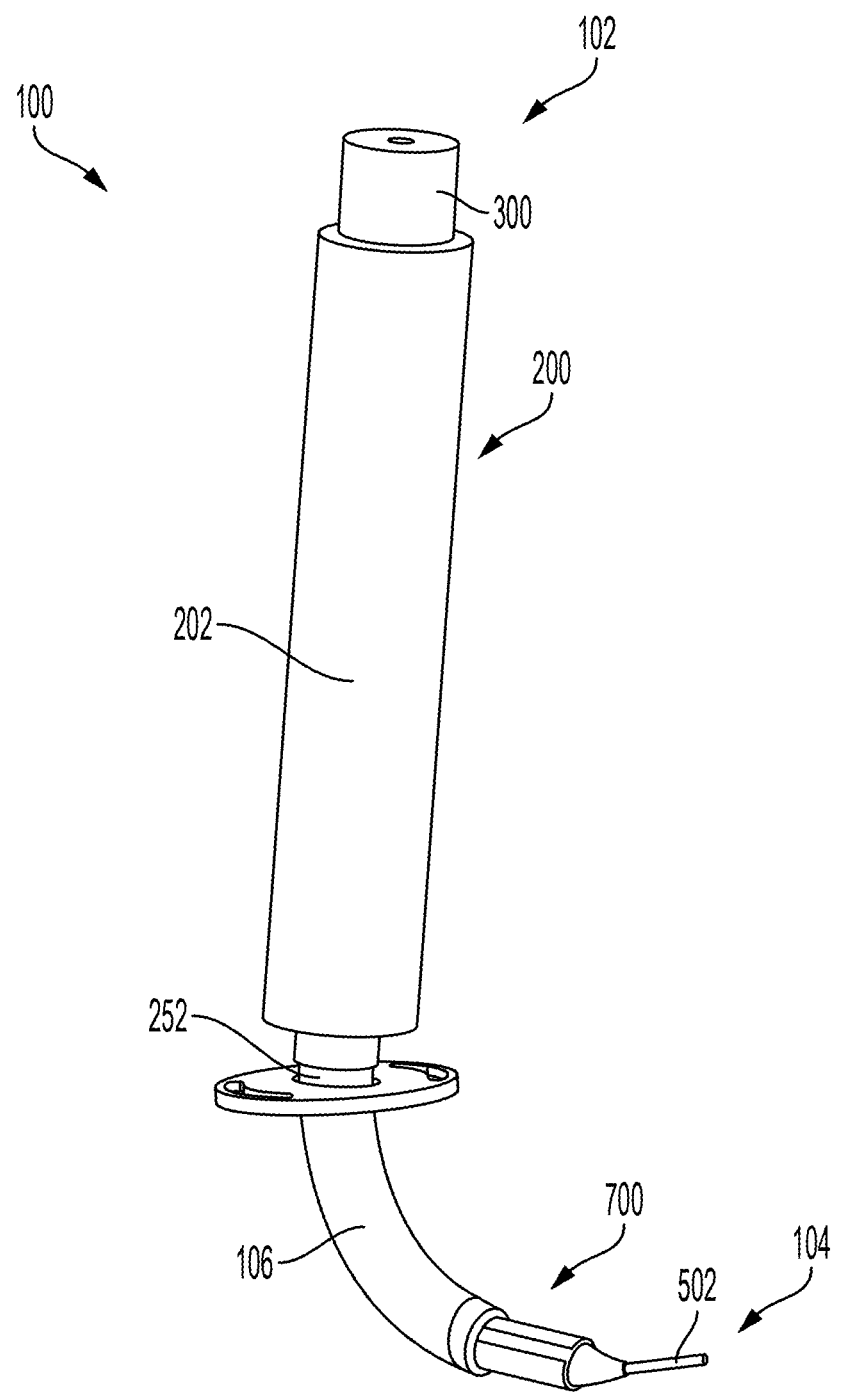
FIG. 3 is a schematic of an exemplary percutaneous dilation tracheostomy device with a preloaded tracheostomy tube.
Figure 4B:
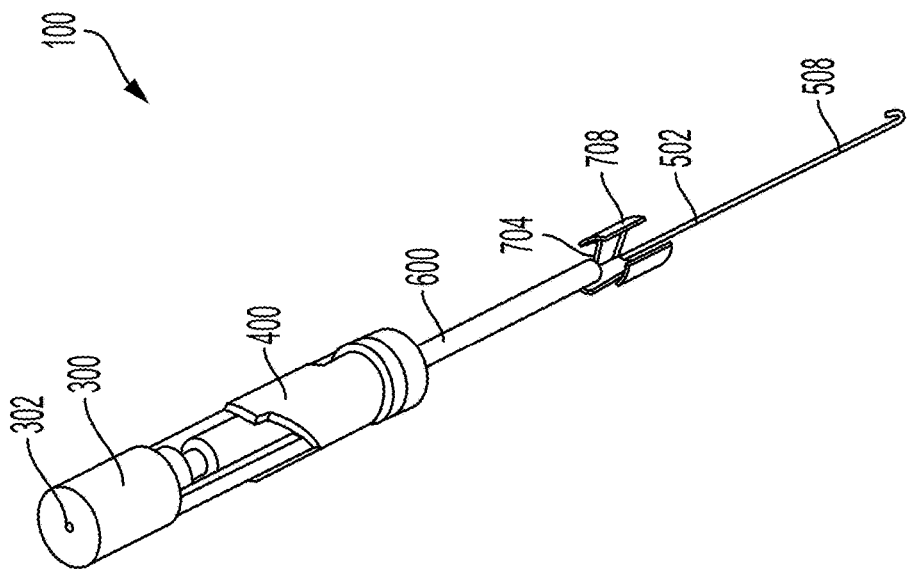
FIG. 4A through FIG. 4C depict the inner components of an exemplary percutaneous dilation tracheostomy device.
Figure 4A:
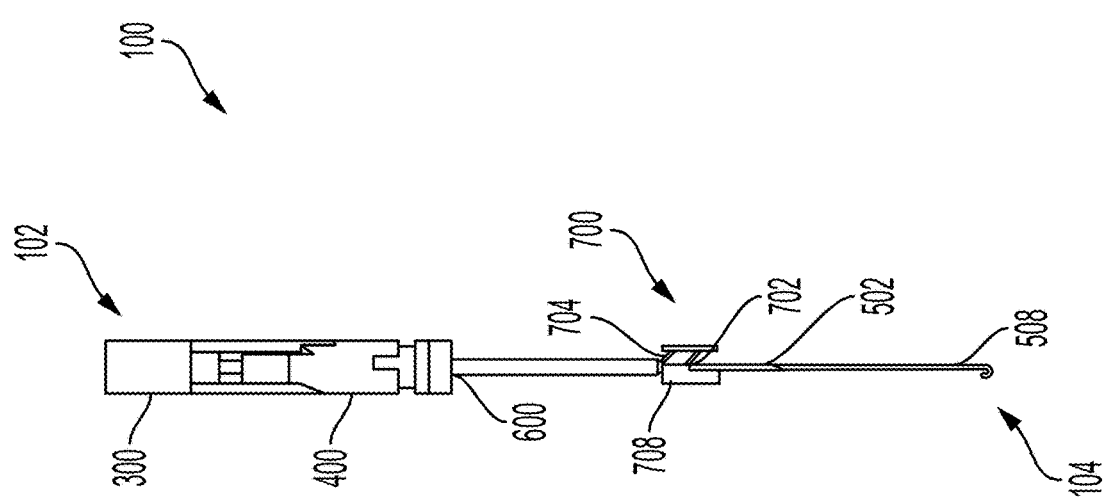
Figure 4C:
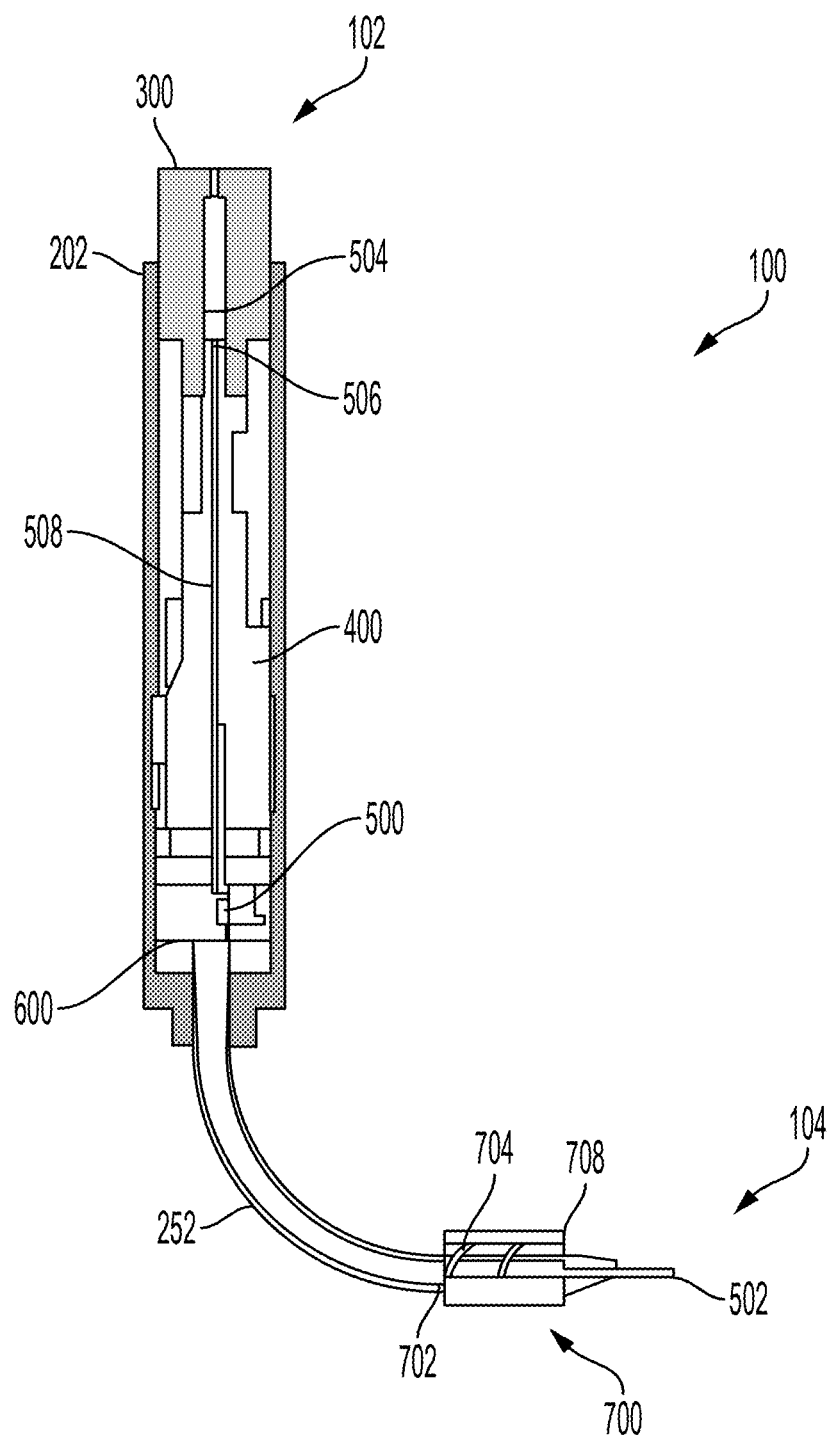

Referring now to FIG. 2 and FIG. 3, an exemplary percutaneous dilation tracheostomy device 100 is depicted having a preloaded tracheostomy tube 106. Device 100 has a proximal end 102 and a distal end 104. Visible from its exterior, device 100 comprises casing 200, plunger 300, dilator 700, and needle 502. FIG. 4A through FIG. 4C reveal the internal components of device 100, further comprising cam 400, plunger connector 600, and j-wire 508.

Referring now to FIG. 5A through FIG. 5D, casing 200 is shown in isolation. Casing 200 comprises a proximal section 202 and a distal section 252. Proximal section 202 has a substantially cylindrical shape having a hollow interior and open proximal and distal ends. Distal section 252 has a substantially tubular, curved shape having a hollow interior, an open proximal end joined to the open distal end of proximal section 202, and an open distal end. Distal section 252 further comprises a plurality of slits 260 accommodating dilator 700, as described elsewhere herein. In some embodiments, casing 200 is generally similar to typical percutaneous tracheostomy casings, such as the Ciaglia Blue Rhino®. Distal section 252 is a curved section that is shaped to accommodate pre-loading of a tracheostomy tube 106 onto device 100 to efficiently introduce tracheostomy tube 106 into the trachea while avoiding damage to the posterior tracheal wall. Distal section 252 is further shaped for an initial dilation of the stoma from approximately 14 Fr to 28 Fr along the curved section.

Figure 6A:
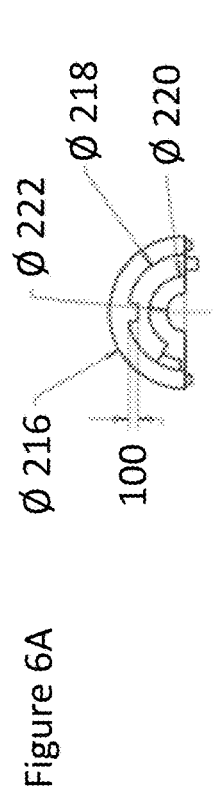
FIG. 6A through FIG. 6C depict half of a proximal section of the casing of an exemplary percutaneous dilation tracheostomy device.
Figure 6B:
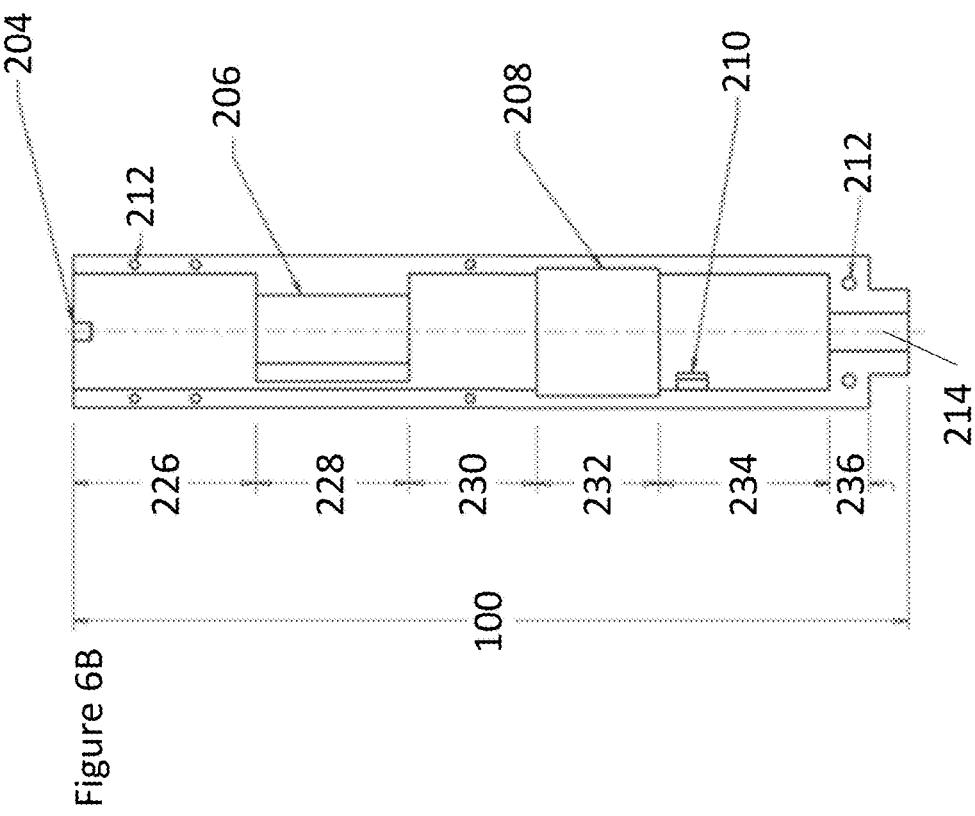
Figure 6C:
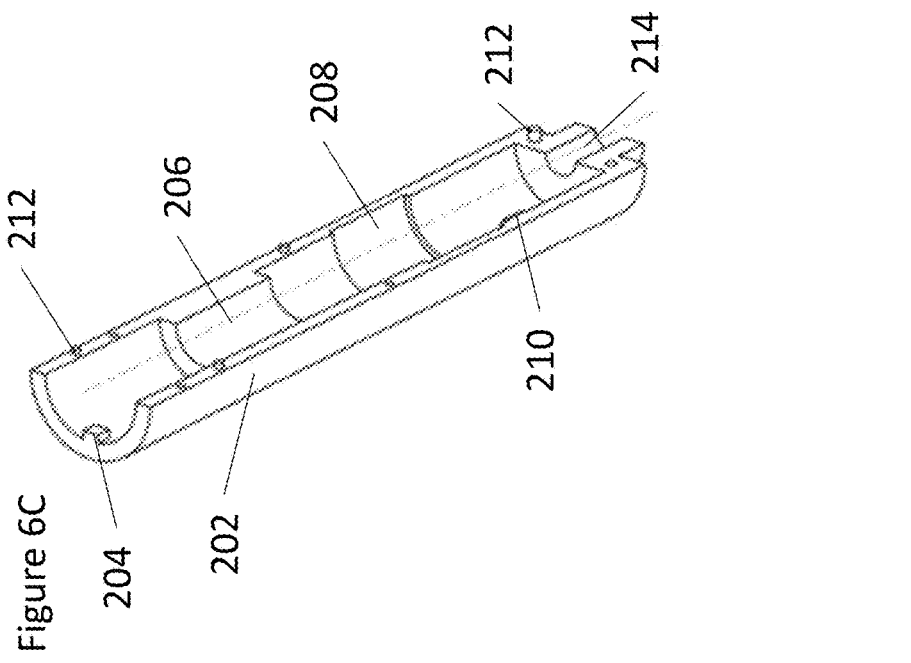
Figure 7A:
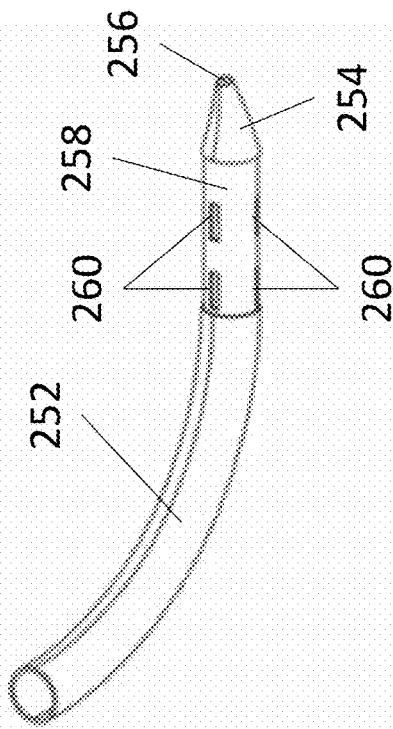
FIG. 7A through FIG. 7D depict the distal section of the casing of an exemplary percutaneous dilation tracheostomy device.
Figure 7B:
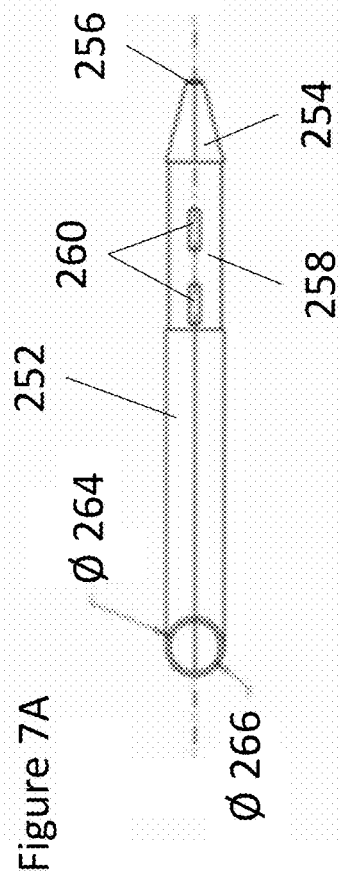
Figure 7C:
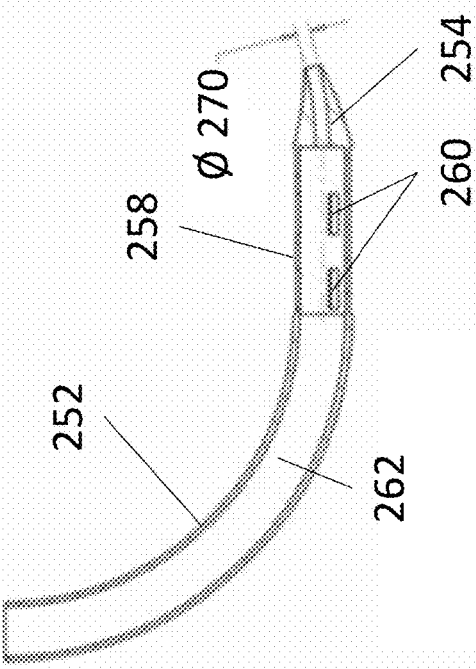
Figure 7D:
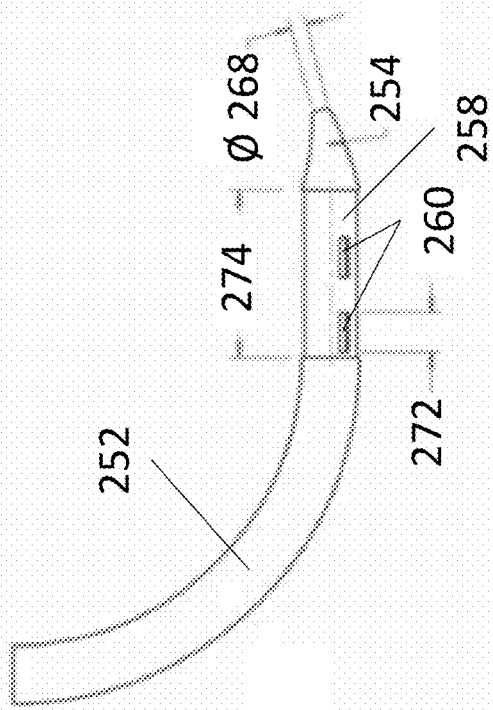
Figure 8B:
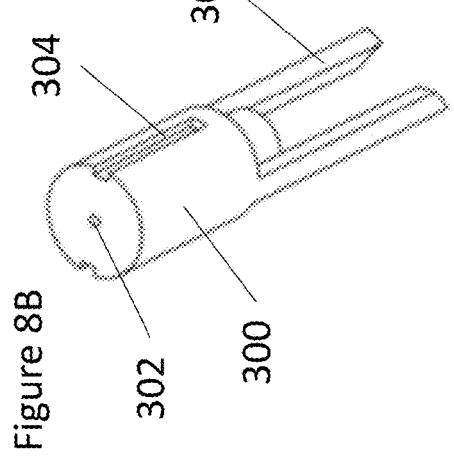
FIG. 8A through FIG. 8D depict the plunger of an exemplary percutaneous dilation tracheostomy device.
Figure 8D:
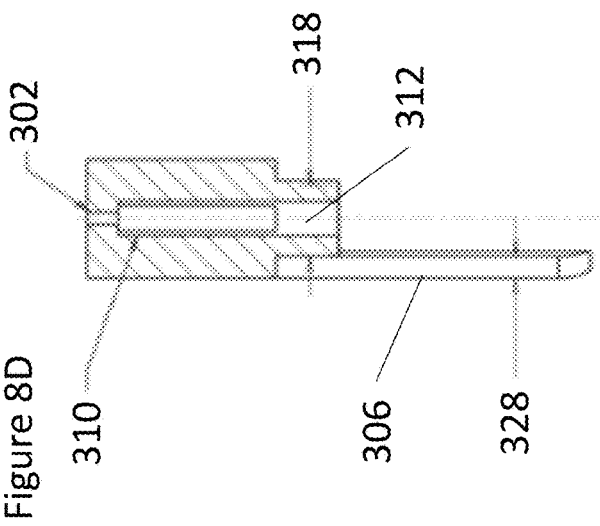
Figure 8A:
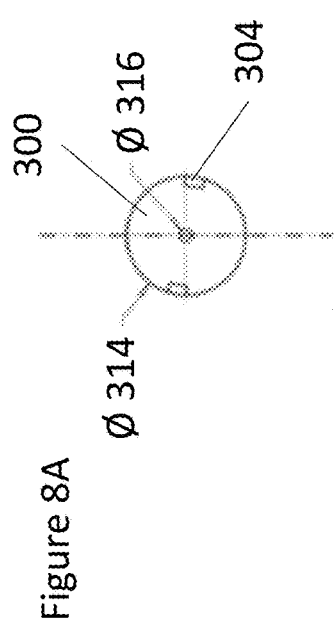
Figure 8C:
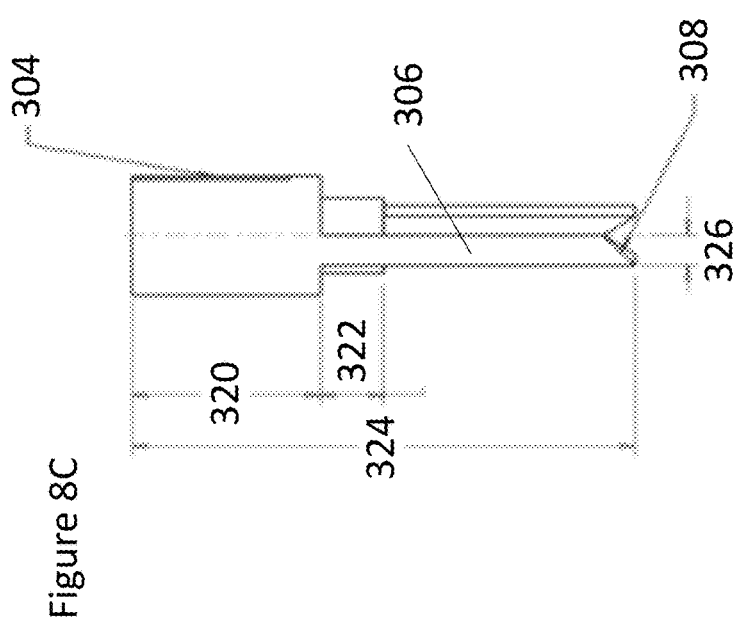
Figure 10B:
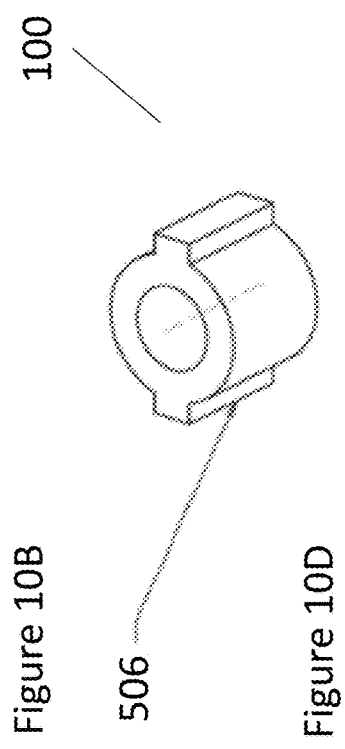
FIG. 10A through FIG. 10F depict the j-wire catch, the j-wire rotational hold, and the needle catch components of an exemplary percutaneous dilation tracheostomy device.
Figure 10D:
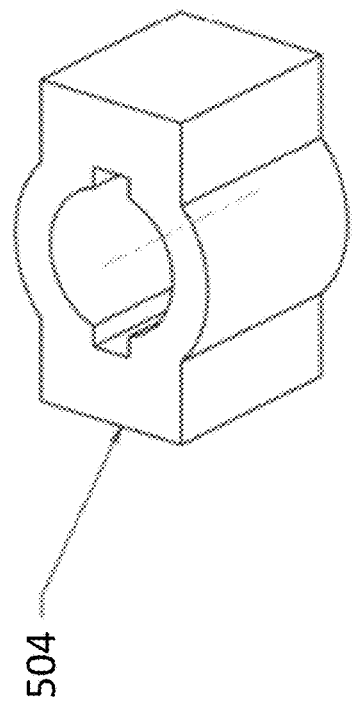
Figure 10F:
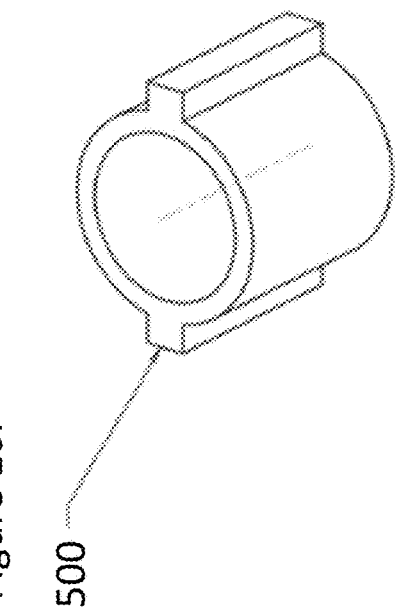
Figure 10A:
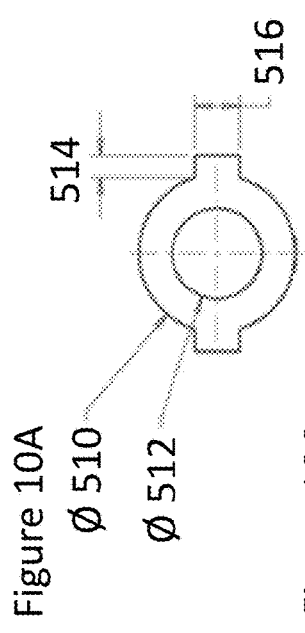
Figure 10C:
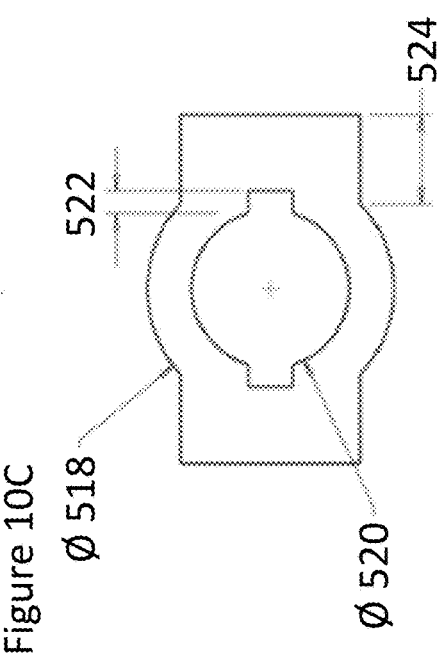
Figure 10E:
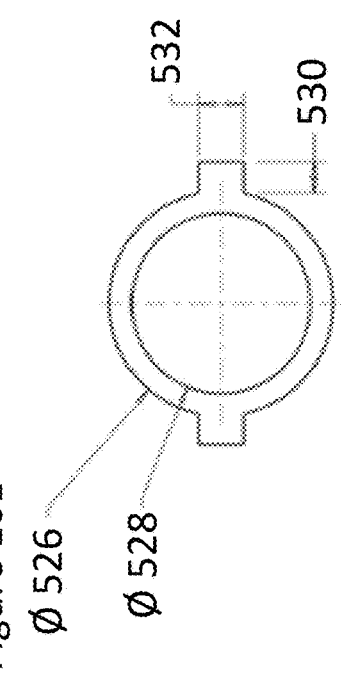

Referring now to FIG. 6A through FIG. 6C, proximal section 202 is described in detail. The interior surface of proximal section 202 comprises several compartments to hold the various internal components of device 100. For example, proximal section 202 comprises a first region 226 holding a portion of plunger 300. Plunger translation hold 204 is provided within first region 226 as a guide to limit movement of plunger 300 in a proximal-distal direction and to prevent plunger 300 from falling out of device 100. Second region 228 comprises plunger rotation hold 206, which includes grooves for prongs 306 of plunger 300 to prevent rotational movement of plunger 300. Third region 230 holds a portion of plunger 300 and cam 400. Fourth region 232 comprises cam spring column 208, which holds a portion of cam 400 and has an increased diameter to accommodate a spring (not pictured). Fifth region 234 holds a portion of cam 400 and plunger connector 600, and includes cam translation catch 210 as a guide to limit the movement of cam 400 in a proximal-distal direction. Sixth region 236 holds a portion of plunger connector 600 and includes lumen 214. In some embodiments, proximal section 202 can be molded as a single unit, along with any internal parts, during fabrication. In other embodiments, proximal section 202 can comprise two or more pieces fitted together by way of tabs 212. In some embodiments, proximal section 202 can further include a locking mechanism configured to temporarily lock the position of an internal component, such as plunger 300.

Proximal section 202 can be constructed from any suitable material, such as a metal or a rigid plastic or polymer. Proximal section 202 can have any suitable dimensions. For example, proximal section 202 can have: an outer diameter between about 20 mm and 30 mm, such as about 25 mm; an inner diameter 208 between about 14 mm and 24 mm, such as about 19 mm; a plunger rotation hold diameter 220 between about 7 mm and 17 mm, such as about 12 mm; a lumen diameter 222 between about 1 mm and 11 mm, such as about 6.27 mm; a plunger translation hold thickness 224 between about 0.5 mm and 2.5 mm, such as about 1.53 mm; a first region 226 height between about 25 mm and 35 mm, such as about 30 mm; a second region 228 height between about 20 mm and 30 mm, such as about 25 mm; a third region 230 height between about 16 mm and 26 mm, such as about 21 mm; a fourth region 232 height between about 15 mm and 25 mm, such as about 20 mm; a fifth region 234 height between about 23 mm and 33 mm, such as about 28 mm; a sixth region 236 height between about 4.5 mm and 8.5 mm, such as about 6.5 mm; and an overall proximal section height 238 between about 127 mm and 147 mm, such as about 137 mm.

Referring now to FIG. 7A through FIG. 7D, distal section 252 is described in detail. Distal section 252 comprises a lumen 262 extending from an open proximal end and a distal tip 254, terminating in a distal aperture 256. Distal section 252 further comprises a recess 258 adjacent to distal tip 254, wherein the length of recess 258 has a diameter that is smaller than outer diameter 264 of distal section 252. Recess 258 further comprises a plurality of elongate slits 260. The number of slits 260 corresponds with the number of struts 704 of dilator 700 as described elsewhere herein, which can be between about 4 and 12, such as 6.

Distal section 252 can be constructed from any suitable material, such as a metal or a rigid plastic or polymer. In some embodiments, distal section 252 can be constructed from a flexible material, such as polyurethane. Distal section 252 can have any suitable dimensions. For example, distal section 252 can have: an outer diameter 264 between about 2 mm and 13 mm, such as about 7.27 mm; an inner diameter 266 between about 1 mm and 12 mm, such as about 6.27 mm; an outer diameter 268 of distal tip 254 between about 1 mm and 3 mm, such as about 2 mm; an inner diameter 270 of distal tip 254 between about 0.5 mm and 2.5 mm, such as about 1.7 mm; a slit length 272 between about 2 mm and 8 mm, such as about 5 mm; and a recess length 274 between about 15 mm and 25 mm, such as about 20.83 mm.

Referring now to FIG. 8A through FIG. 8D, plunger 300 is described in detail. Plunger 300 comprises a substantially cylindrical proximal portion having two or more prongs 306 extending from its proximal portion in a distal direction. Plunger 300 comprises a lumen 312 extending through the height of plunger 300, lumen 312 being connected to syringe port 302 at a proximal end and having an open distal end. Lumen 312 further comprises j-wire groove 310 embedded in its inner surface for guiding the movement of j-wire catch 506 in a proximal-distal direction. In some embodiments, lumen 312 comprises a compressed spring loaded between syringe port 302 and j-wire catch 506. Plunger 300 comprises one or more plunger translation grooves 304 embedded in its exterior, wherein each plunger translation groove 304 is sized to fit a plunger translation hold 204 of proximal section 202. Each prong 306 terminates in a prong interface 308 at its distal end. Prong interface 308 has an angled construction configured to mate with first cam interface 402 and second cam interface 404, as described elsewhere herein.

Plunger 300 can be constructed from any suitable material, such as a metal or a rigid plastic or polymer. Plunger 300 can have any suitable dimensions. For example, plunger 300 can have: an outer diameter 314 between about 14 mm and 23 mm, such as about 19 mm; a syringe port diameter 316 between about 1 mm and 3 mm, such as about 2 mm; a diameter 318 between about 6 mm and 16 mm, such as about 11.2 mm; a first region 320 height between about 25 mm and 35 mm, such as about 30 mm; a second region 322 height between about 5 mm and 15 mm, such as about 10 mm; a plunger height 324 between about 70 mm and 90 mm, such as about 80 mm; a prong width 326 between about 2 mm and 6 mm, such as about 4.75 mm; and a prong thickness 328 between about 1 mm and 5 mm, such as about 3.5 mm.

Referring now to FIG. 9A through FIG. 9D, cam 400 is described in detail. Cam 400 comprises a substantially cylindrical shape having several exterior features configured to mate with and actuate the various components of device 100. At a first region 432, cam 400 comprises a diameter 428 sized to fit within the open distal end of plunger 300 for additional stability. At a second region 434, cam 400 comprises a diameter 426 sized to fit between prongs 306 of plunger 300. In some embodiments, second region 434 further comprises a spring wound around cam 400 and touching the distal end of plunger 300. At a third region 436, cam 400 comprises spring hold 408, which is configured to engage a spring within cam spring column 208 of proximal section 202. Third region 436 further comprises first cam interface 402 and second cam interface 404. First cam interface 402 and second cam interface 404 are angled surfaces that are in alignment with the angle of prong interfaces 308, such that prong interfaces 308 are configured to slide along first cam interface 402 and engage second cam interface 404. Third region 436 further comprises translation groove 410 embedded in its exterior, wherein translation groove 410 is sized to fit cam translation catch 210 of proximal section 202. At a fourth region 438, cam 400 comprises rotation groove 412 embedded in its exterior, wherein rotation groove 412 is sized to fit cam translation catch 210 of proximal section 202. At a fifth region, cam 400 comprises plunger connector flange 414. At a sixth region 440 and a seventh region 442, cam 400 comprises plunger connector plug 416, which is configured to engage with plunger connector 600, as described elsewhere herein. Cam 400 further comprises lumen 422 extending between an open proximal end and an open distal end, the proximal end having a j-wire groove 418 and the distal end having a needle groove 420. In some embodiments, needle groove 420 is helix-shaped, such that a needle catch 500 moving through needle groove 420 is configured to rotate cam 400.

Cam 400 can be constructed from any suitable material, such as a metal or a rigid plastic or polymer. Cam 400 can have any suitable dimensions. For example, cam 400 can have: a diameter 424 between about 14 mm and 24 mm, such as about 19 mm; a diameter 426 between about 7 mm and 17 mm, such as about 12 mm; a diameter 428 between about 3 mm and 8 mm, such as about 5.5 mm; a diameter 430 between about 12 mm and 22 mm, such as about 17 mm; a first region 432 height between about 25 mm and 35 mm, such as about 30 mm; a second region 434 height between about 15 mm and 25 mm, such as about 20 mm; a third region 436 height between about 30 mm and 40 mm, such as about 35 mm; a rotation groove height 438 between about 3 mm and 7 mm, such as about 5 mm; a flange height 440 between about 3 mm and 7 mm, such as about 5 mm; a plug height 442 between about 3 mm and 7 mm, such as about 5 mm; a fourth region 444 height between about 60 mm and 70 mm, such as about 65 mm; a fifth region height between about 25 mm and 35 mm, such as about 30 mm; a sixth region height between about 3 mm and 7 mm, such as about 5 mm; and a cam height 450 between about 90 mm and 110 mm, such as about 102 mm.

Figure 11:
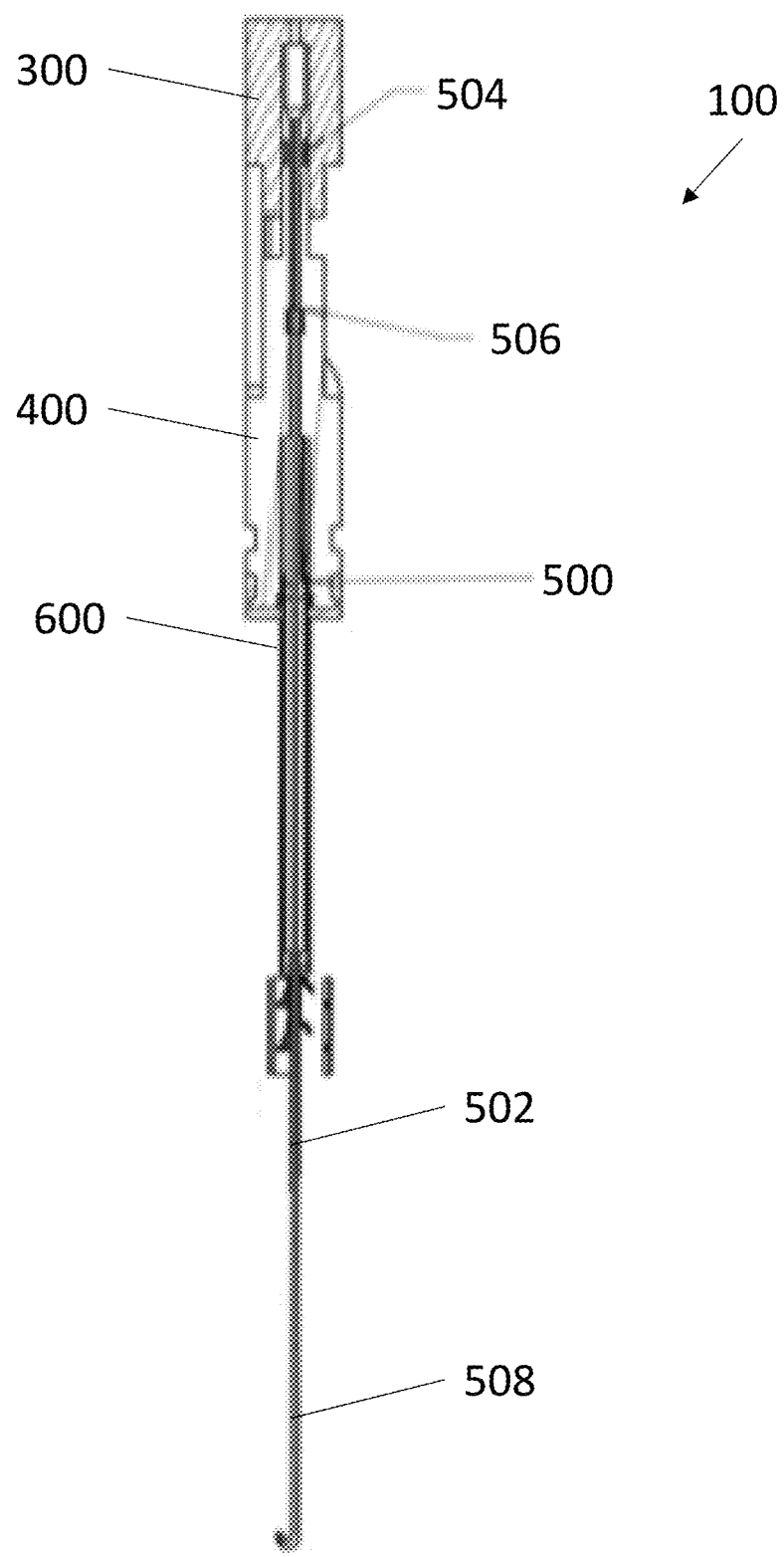
FIG. 11 is a cross-sectional side view of an exemplary percutaneous dilation tracheostomy device showing the locations of the j-wire catch, the j-wire rotational hold, and the needle catch components.
Figure 12B:
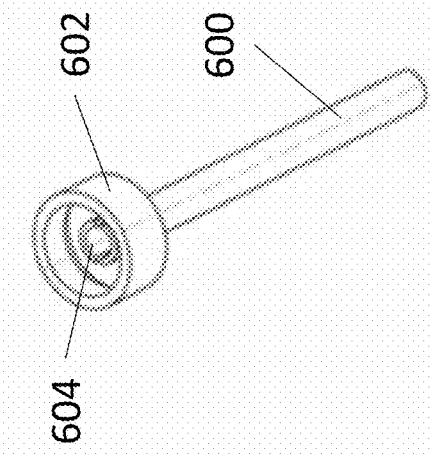
FIG. 12A through FIG. 12D depict the plunger connector of an exemplary percutaneous dilation tracheostomy device.
Figure 12A:
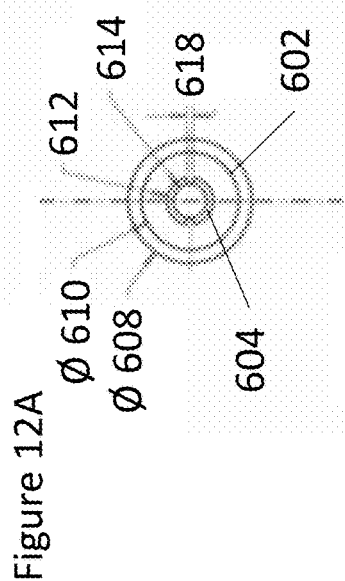
Figure 12D:
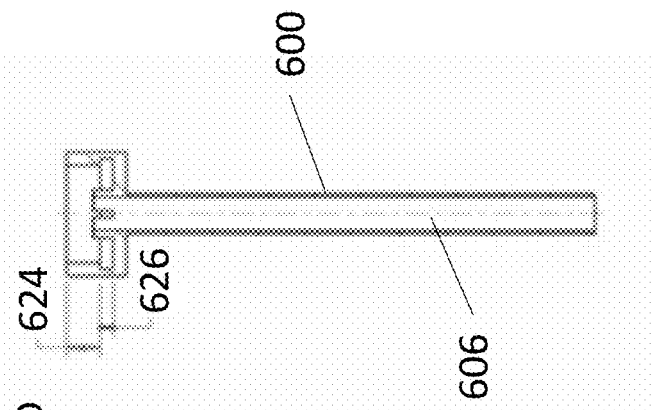
Figure 12C:
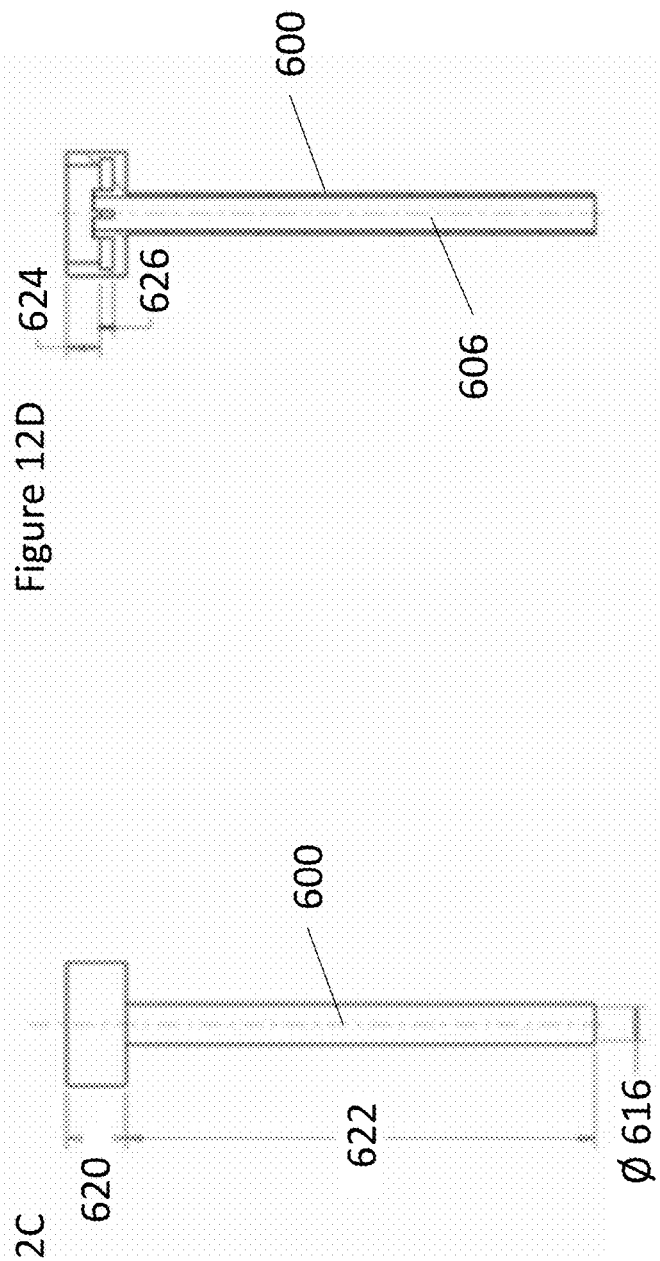

Referring now to FIG. 10A through FIG. 10F, needle catch 500, j-wire rotational hold 504, and j-wire catch 506 are described in detail. J-wire catch 506 comprises a hollow cylindrical shape having opposing parallel tabs attached to its exterior. J-wire catch 506 is sized to fit within j-wire groove 418 of cam 400 and j-wire groove 310 of plunger 300. J-wire catch 506 is configured to secure the distal end of a flexible j-wire 508, such that the positioning of j-wire 508 can be manipulated by repositioning j-wire catch 506 within device 100. J-wire rotation hold 504 comprises a substantially cylindrical shape having a hollow interior sized to fit j-wire catch 506 and opposing parallel tabs attached to its exterior. J-wire rotation hold 504 is sized to fit within lumen 312 of plunger 300, as shown in FIG. 11. J-wire rotation hold 504 is a stationary component that prevents rotation of j-wire catch 506 for the duration that j-wire catch 506 is held within its interior. Needle catch 500 comprises a hollow cylindrical shape having opposing parallel tabs attached to its exterior. Needle catch 500 is sized to fit within needle groove 420 of cam 400 and needle catch socket 604 of plunger connector 600, as described elsewhere herein. Needle catch 500 is configured to secure the distal end of a flexible needle 502, such that the positioning of needle 502 can be manipulated by repositioning needle catch 500 within device 100.

Needle catch 500, j-wire rotational hold 504, and j-wire catch 506 can each be constructed from any suitable material, such as a metal or a rigid plastic or polymer. Needle catch 500, j-wire rotational hold 504, and j-wire catch 506 can have any suitable dimensions. For example, needle catch 500 can have: an outer diameter 526 between about 3 mm and 7 mm, such as about 5 mm; an inner diameter 528 between about 2 mm and 6 mm, such as about 4 mm; a tab thickness 530 between about 0.5 and 1 mm, such as about 0.7 mm; and a tab width 532 between about 0.7 and 1.5 mm, such as about 1 mm. J-wire rotational hold 504 can have: an outer diameter 518 between about 3.5 mm and 7.5 mm, such as about 5.5 mm; an inner diameter 520 between about 1.5 mm and 5.5 mm, such as about 3.5 mm; a tab slot thickness 522 between about 0.1 mm and 1 mm, such as about 0.5 mm, and a tab thickness 524 between about 1 mm and 3 mm, such as about 2 mm. J-wire catch 506 can have: an outer diameter 510 between about 1.5 mm and 5.5 mm, such as about 3.5 mm; an inner diameter 512 between about 1 mm and 3 mm, such as about 2 mm; a tab thickness 514 between about 0.1 mm and 1 mm, such as about 0.5 mm, and a tab width 516 between about 0.5 mm and 1.5 mm, such as about 1 mm.

Referring now to FIG. 12A through FIG. 12D, plunger connector 600 is described in detail. Plunger connector 600 comprises a lumen 606 extending between a proximal cam socket 602, through an elongate and flexible tubular section, and terminating in a distal opening. Cam socket 602 is configured to engage plunger connector plug 416 of cam 400. Cam socket 602 comprises needle catch socket 604 at its center, which is configured to engage needle catch 500. In some embodiments, plunger connector 600 comprises a compressed spring loaded between needle catch socket 604 and a needle catch 500.

Plunger connector 600 can be constructed from any suitable material, such as a flexible plastic or polymer configured to flex with and move through distal section 252 of casing 200. Plunger connector 600 can have any suitable dimensions. For example, plunger connector 600 can have: an outer diameter 608 of cam socket 602 between about 14 mm and 24 mm, such as about 19 mm; an inner diameter 610 of cam socket 602 between about 10 mm and 20 mm, such as about 15 mm; an outer diameter 612 of needle catch socket 604 between about 2 mm and 5 mm, such as about 3.6 mm; an inner diameter 614 of needle catch socket 604 between about 1 mm and 4 mm, such as about 2.6 mm; a lumen diameter 616 between about 3 mm and 7 mm, such as about 5.2 mm; a tab slot width 618 between about 0.5 mm and 1.5 mm, such as about 1 mm; a first region height 620 between about 5 mm and 13 mm, such as about 9 mm; a second region 622 height between about 60 mm and 80 mm, such as about 72 mm; a third region 624 height between about 3 mm and 7 mm, such as about 5 mm, and a fourth region 626 height between about 1 mm and 3 mm, such as about 2 mm.

Figure 13B:
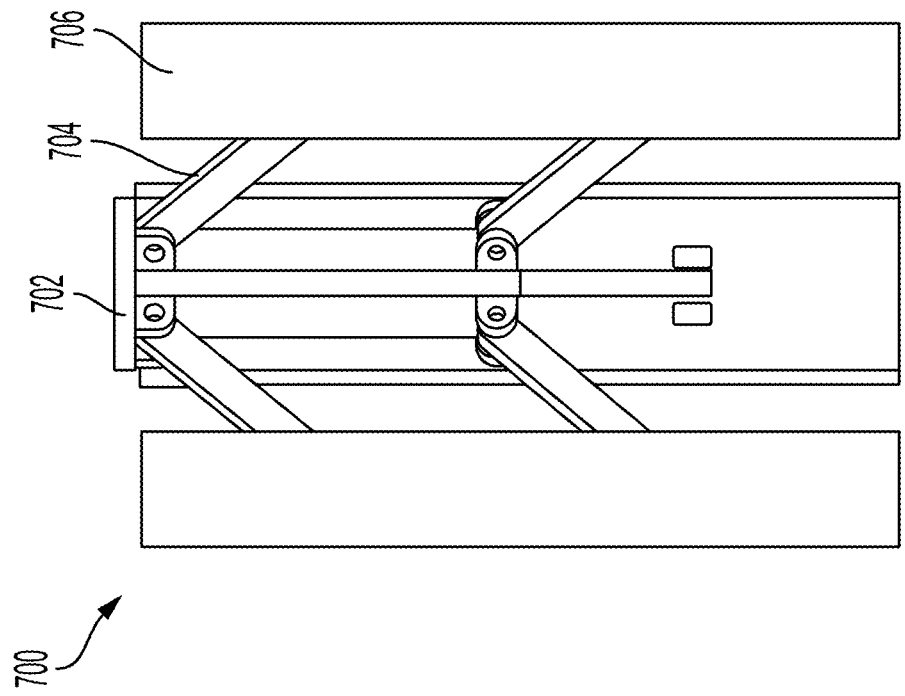
FIG. 13A and FIG. 13B depict the dilator of an exemplary percutaneous dilation tracheostomy device.
Figure 13A:
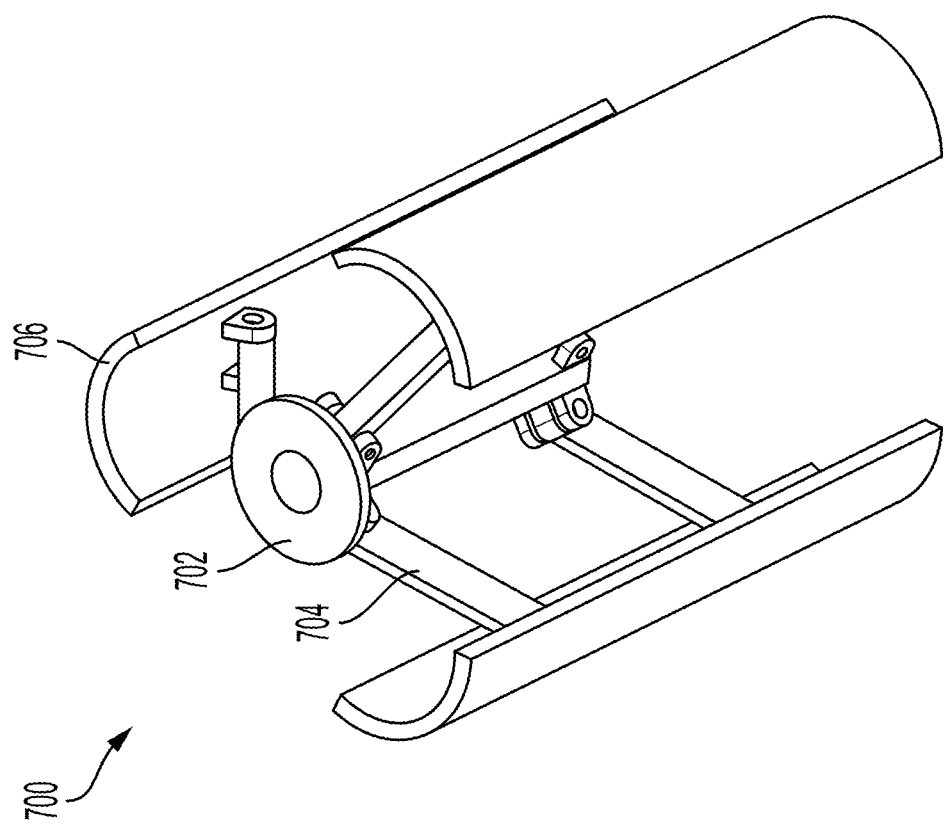

Referring now to FIG. 13A and FIG. 13B, dilator 700 is depicted. Dilator 700 comprises a plurality of wall members 706 hingedly connected to a central column 702 by way of a plurality of struts 704. Dilator 700 is assembled in device 100 such that column 702 is seated within lumen 262 of distal section 252, each strut 704 attached to column 702 passes through a slit 260, and each strut 704 attaches to a wall member 706 exterior to distal section 252. Dilator 700 has a closed configuration and an expanded configuration, wherein the closed configuration brings the plurality of wall members 706 together edge to edge to form a substantially cylindrical shape within recess 258, and the open configuration (shown in FIG. 13A and FIG. 13B) expands the plurality of wall members 706 away from each other radially. In some embodiments, the expansion of wall members 706 increases the effective diameter of dilator 700 from about 3 mm to about 10 mm.

Referring now to FIG. 14A through FIG. 14D, column 702 is described in detail. Column 702 comprises a substantially solid polyhedral shape having a proximal end, a distal end, and a plurality of faces supporting a plurality of hinges 712. Column 702 comprises lumen 714 running from a proximal head 710 to a distal open end. In the embodiment depicted, column 702 has three faces, each face supporting a proximal pair of hinges 712 and a distal pair of hinges 712, for a total of twelve hinges 712. It should be understood that column 702 can have as many faces and as many hinges 712 as desired, including but not limited to combinations such as: two faces with a proximal and distal pair of hinges 712 per face totaling eight hinges 712; four faces with a proximal and distal pair of hinges 712 per face totaling sixteen hinges 712; five faces with a proximal and distal pair of hinges 712 per face totaling twenty hinges 712; and six faces with a proximal and distal pair of hinges 712 per face totaling twenty four hinges 712. Column 702 can further include facet surfaces between each adjacent face.

Column 702 can be constructed from any suitable material, such as a metal or a rigid plastic or polymer. Column 702 can have any suitable dimensions. For example, column 702 can have: a head diameter 716 between about 3 mm and 6 mm, such as about 4.5 mm; a lumen diameter 718 between about 1 mm and 2 mm, such as about 1.7 mm; a head thickness 720 between about 0.1 mm and 1 mm, such as about 0.5 mm; a hinge separation 722 between about 5 mm and 11 mm, such as about 8 mm; a facet width 724 between about 0.5 mm and 1 mm, such as about 0.73 mm; a face width 726 between about 1 mm and 2 mm, such as about 1.73 mm; a column length 728 between about 8 mm and 12 mm, such as about 10.67 mm; a hinge height 730 between about 0.5 mm and 1.5 mm, such as about 1 mm; and a hinge hole diameter 732 between about 0.1 mm and 1 mm, such as about 0.5 mm.

Figure 15B:
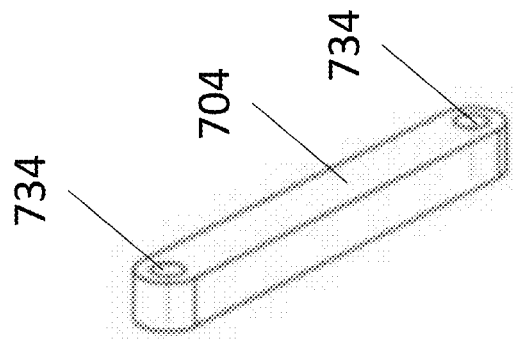
FIG. 15A through FIG. 15C depict the strut of the dilator of an exemplary percutaneous dilation tracheostomy device.
Figure 15A:
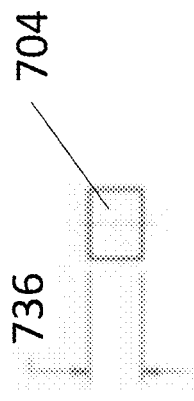
Figure 15C:
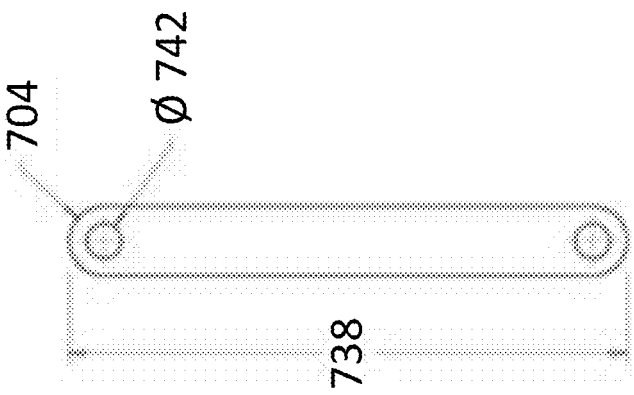
Figure 16B:
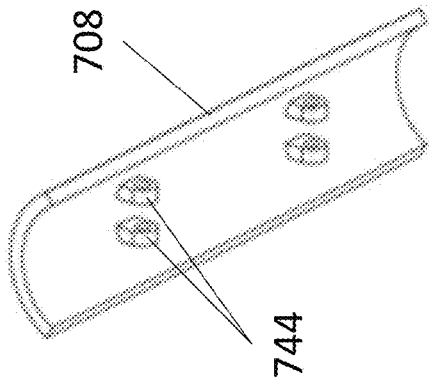
FIG. 16A through FIG. 16D depict the wall member of the dilator of an exemplary percutaneous dilation tracheostomy device.
Figure 16D:
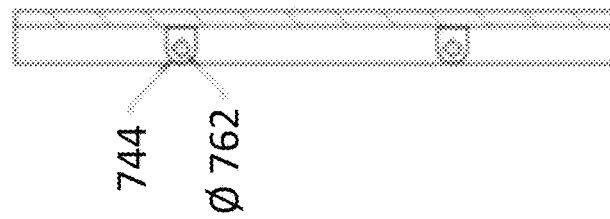
Figure 16A:
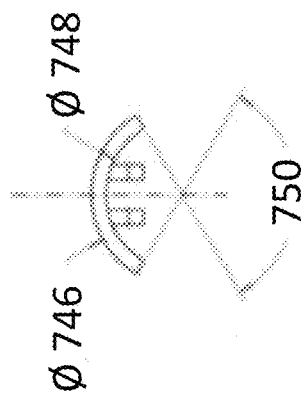
Figure 16C:
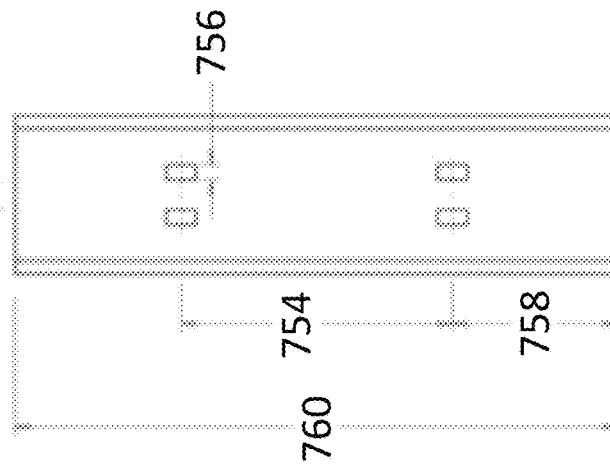

Referring now to FIG. 15A through FIG. 15C, strut 704 is described in detail. Strut 702 has an elongate rectangular shape and cross-section and rounded ends each having a hinge hole 734. Hinge hole 734 is sized to hingedly connect to a pair of hinges 712 of column 702 and a pair of hinges 744 of wall member 708, such as by a hinge pin. At least two struts 704 thereby hingedly connect column 702 to each wall member 708.

Strut 704 can be constructed from any suitable material, such as a metal or a rigid plastic or polymer. Strut 704 can have any suitable dimensions. For example, strut 704 can have: a strut thickness 736 between about 0.5 and 1 mm, such as about 0.75 mm; a strut length 738 between about 5 mm and 11 mm, such as about 8 mm; and a hinge hole diameter 742 between about 0.3 mm and 1 mm, such as about 0.5 mm.

Referring now to FIG. 16A through FIG. 16D, wall member 708 is described in detail. Each wall member 708 has a thickness that is substantially the same as the depth of recess 258 of distal section 252, such that wall members 708 can be seated in recess 258 to be flush against the outer diameter 264 of distal section 252. Each wall member 708 curves along arc 750, such that a plurality of wall members 708 is configured to join edge to edge to form a substantially cylindrical shape. The degree of arc 750 thereby depends on the number of wall members 708 used to form the 360° of a substantially cylindrical shape. For example, two wall members 708 can each have an arc 750 of about 180°; three wall members 708 can each have an arc 750 of about 120°; four wall members 708 can each have an arc 750 of about 90°; five wall members 708 can each have an arc 750 of about 72°; six wall members 708 can each have an arc 750 of about 60°; etc. Each wall member 708 comprises a proximal pair and a distal pair of hinges 744, similar to the arrangement of hinges 712 on column 702.

Wall member 708 can be constructed from any suitable material, such as a metal or a rigid plastic or polymer. Wall member 708 can have any suitable dimensions. For example, wall member 708 can have: a combined outer diameter 746 of between about 4 mm and 8 mm, such as about 6.1 mm; a combined inner diameter 748 between about 3 mm and 7 mm, such as about 5.1 mm; a hinge spacing 752 between about 0.5 mm and 1.5 mm, such as about 1 mm; a hinge separation 754 between about 5 mm and 13 mm, such as about 9 mm; a hinge thickness 756 between about 0.3 mm and 1 mm, such as about 0.5 mm; a wall overhang 758 between about 3 mm and 8 mm, such as about 5.5 mm; a wall member height 760 between about 15 mm and 25 mm, such as about 20 mm; and a hinge hole diameter between about 0.3 mm and 1 mm, such as about 0.5 mm.

Figure 17:
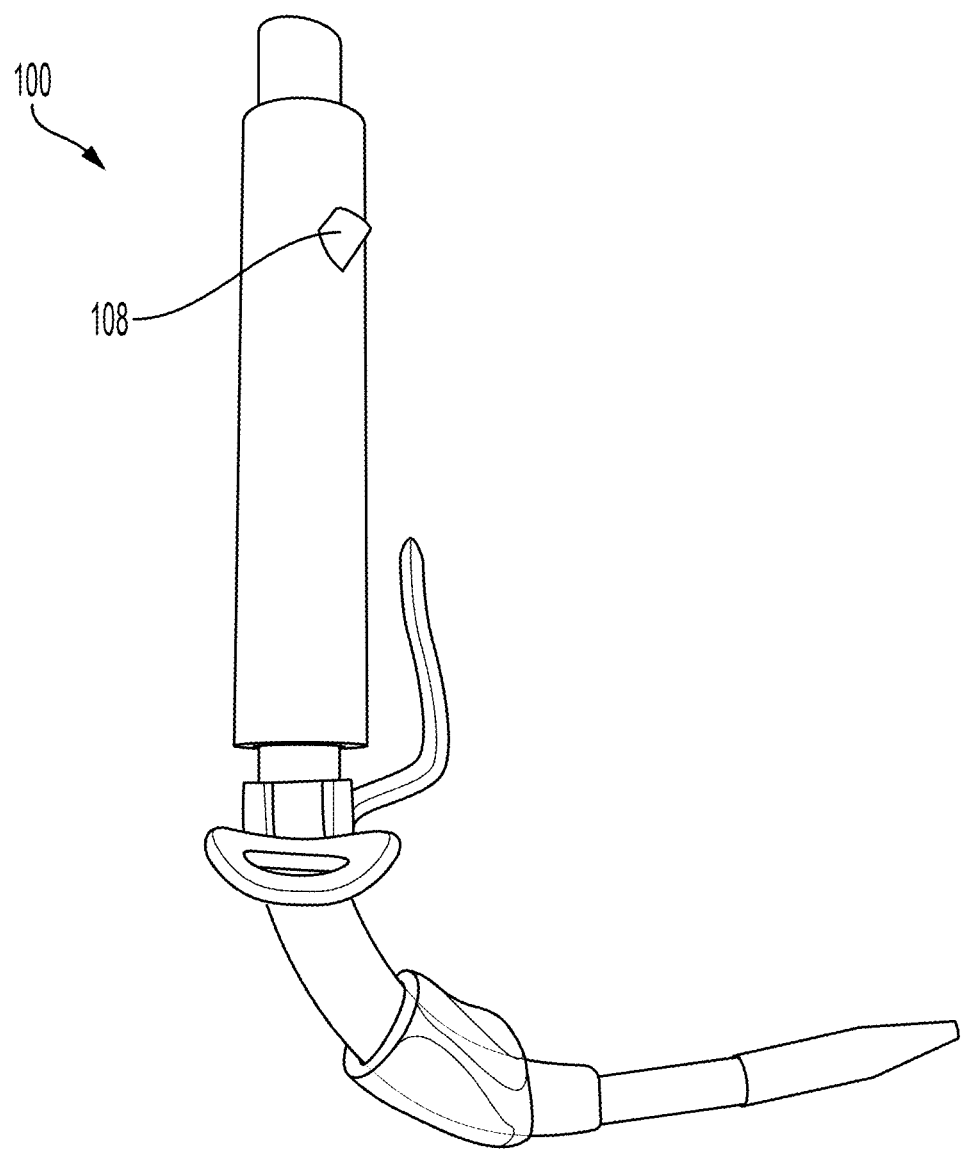
FIG. 17 is a photograph of a side view of an exemplary percutaneous dilation tracheostomy device having a side port.

In various embodiments, device 100 can further comprise one or more modifications to enhance its performance. For example, in some embodiments device 100 can include a side port 108 positioned on proximal section 202 of casing 200 (FIG. 17). Side port 108 is fluidly connected to distal section 252 of casing 200 or to needle 502. In some embodiments, side port 108 is configured to provide a continuous flow of a source of fluid or gas through needle 502, such as a source of oxygen or air. Side port 108 can be compatible with typical gas or fluid couplings to connect to a source of fluid or gas. Side port 108 can be positioned perpendicular to the axis of proximal casing 202, or angled to minimize interference between any connected tubing, a patient, and/or an operator. Thus, side port 108 can reduce the likelihood of complications associated with hypoxia (i.e., lack of oxygen) while inserting device 100 (e.g., which may be related to a partial or complete airway obstruction that occurs while placing the standard percutaneous device). Side port 108 can also be compatible with an end tidal CO2 detector. An end tidal CO2 detector is a monitor generally used to confirm airway placement of an endotracheal and tracheostomy tube. Thus, side port 108 can allow real-time confirmation of device placement within a patient and reduce the risk of a misplaced tracheostomy tube.

The function of percutaneous dilation tracheostomy device 100 is now described. Syringe port 302 and lumen 312 of plunger 300, lumen 422 of cam 400, lumen 606 of plunger connector 600, lumen 714 of dilator 700, and lumen 262 and distal aperture 256 of casing 200 are in fluid connection. A needle 502 having a lumen is thereby able to pass through each of the structures listed above, and a syringe attached to syringe port 302 has fluid access to the distal end of needle 502, enabling the syringe to perform a bubble test.

Device 100 is configured to perform several actions through the depression of plunger 300. In summary, a first depression of plunger 300 simultaneously retracts needle 502 into device 100 while extending j-wire 508. Upon releasing plunger 300, a second depression of plunger 300 expands dilator 700.

The first depression of plunger 300 pushes prongs 306 in a distal direction to press prong interfaces 308 against the angled surface of first cam interface 402. As prongs 306 continue to advance in a distal direction, the action of prong interfaces 308 pressing against the angled surface of first cam interface 402 causes cam 400 to perform a first rotation. The first rotation of cam 400 is guided by rotation groove 412 moving along cam translation catch 210. Cam 400 can be rotated between about 15° and 180° from its starting position, such as about 60°. As cam 400 rotates, j-wire groove 418 at the proximal end of cam 400 is placed in alignment with j-wire catch 506 and needle groove 420 at the distal end of cam 400 is placed in alignment with needle catch 500. The alignment permits j-wire catch 506 to be pushed distally from plunger 300 into j-wire groove 418 by way of the compressed spring in plunger 300, pushing j-wire 508 out of the distal end of device 100. In some embodiments, the alignment between j-wire catch 506 and j-wire groove 418 occurs after a 30° rotation of cam 400. The alignment also permits needle catch 500 to be pushed proximally from plunger connector 600 into needle groove 420 by way of the compressed spring in plunger connector 600, retracting needle 502 from the distal end of device 100. In some embodiments, the alignment between needle catch 500 and needle groove 420 occurs upon completion of the first rotation of cam 400. Releasing plunger 300 springs plunger 300 to its starting position, which releases prongs 306 from cam 400 and permits the proximal movement of needle catch 500 within needle groove 420 to perform a second rotation of cam 400. The second rotation of cam 400 aligns second cam interface 404 with prongs 306, and also aligns translation groove 410 with cam translation catch 210. In some embodiments, the second rotation is about 30°.

The second depression of plunger 300 pushes prongs 306 in a distal direction to press prong interfaces 308 against the angled surface of second cam interface 404. Due to the length of second cam interface 404, the advancement of prongs 306 and prong interfaces 308 in a distal direction pushes cam 400 in a distal direction without rotating cam 400. The distal advancement of cam 400 is guided by translation groove 410 moving along cam translation catch 210. As cam 400 advances, plunger connector 600 is pushed through the curved distal section 252 of casing 200, whereupon the distal end of plunger connector 600 pushes against head 710 of column 702 and advances column 702 in a distal direction. As column 702 advances in a distal direction, the movement of each strut 704 attached to column 702 is constrained by each of the slits 260. Each strut 704 synchronously expands outwards, thereby expanding each wall member 706 outwards. As the expansion of dilator 700 is directly linked to the second depression of plunger 300, plunger 300 can provide feedback based on the resistance felt in depressing plunger 300. For example, increasing resistance to depressing plunger 300 generally indicates increasing resistance (e.g., strength) at dilator 700, such as from the tracheal wall.

The various components of device 100 can be constructed from materials having sufficient strength, flexibility, machinability, surface finish, and biocompatibility for medical use, such as for emergency tracheotomies. Furthermore, the materials and configurations of the device are generally selected for fabrication costs, ease of use, and accessibility. For example, in some embodiments, device 100 can be provided in a basic configuration having a cheap and simple construction comprising only a casing 200 housing a plunger 300 directly engaging a dilator 700, such that a single depression of plunger 300 is configured to directly expand dilator 700 as described elsewhere herein.

The various components of device 100 can be manufactured according to many methods, including additive manufacturing (e.g., 3D printing). Other types of manufacturing can be used, such as injection molding, casting, machining, and the like. For example, components substantially comprising a metal may be milled from a larger block of metal or may be cast from molten metal. Likewise, components substantially comprising a plastic or polymer may be milled from a larger block, cast, or injection molded.

Methods of Percutaneous Dilation Tracheostomy

The present invention further includes methods of using the percutaneous dilation tracheostomy devices of the present invention. The devices are configured to incorporate several components that are typically separate, simplifying three major steps of emergency tracheotomies: puncture of the trachea, dilation of the stoma and introduction of the tracheostomy tube.

Figure 18:
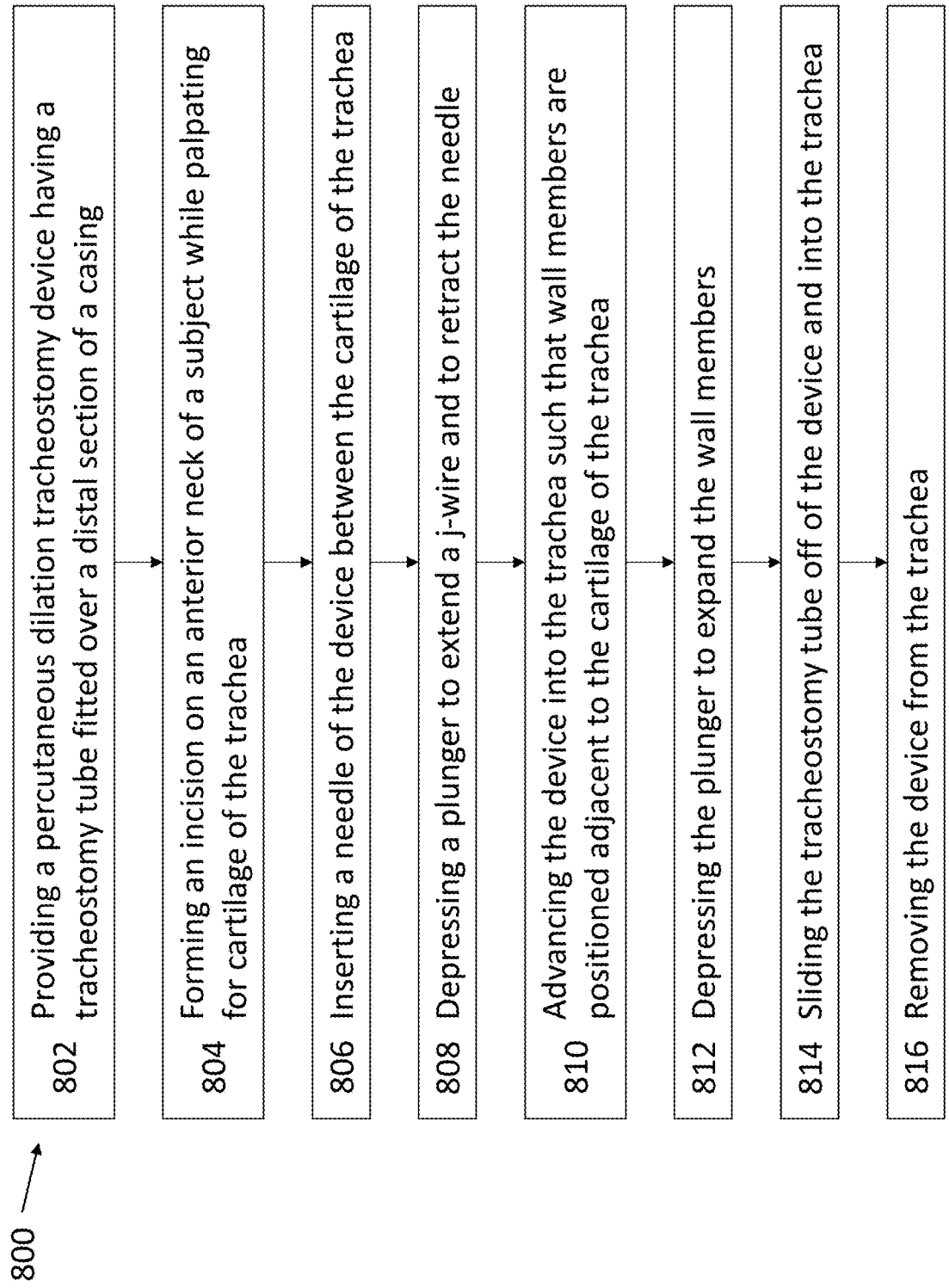
FIG. 18 is a flowchart listing the steps of an exemplary method of inserting a tracheostomy tube into a patient using a percutaneous dilation tracheostomy device.
Figure 19:
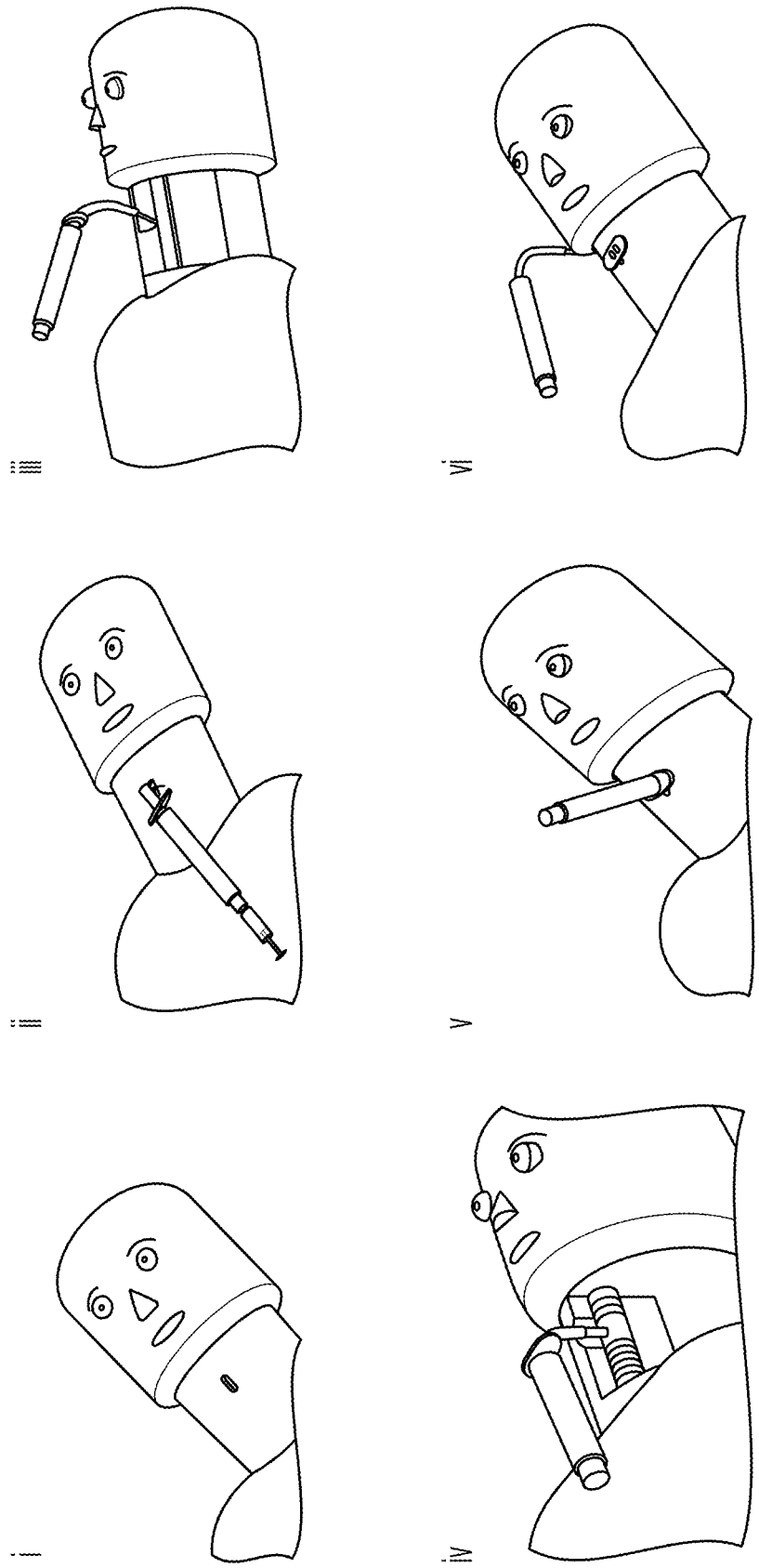
FIG. 19 is an illustration of an exemplary method of using a percutaneous dilation tracheostomy device.

Referring now to FIG. 18, an exemplary method 800 is depicted. Method 800 begins with step 802, wherein a percutaneous dilation tracheostomy device of the present invention is provided having a tracheostomy tube fitted over a distal section of the casing. In step 804, an incision is formed on an anterior neck of a subject while palpating for cartilage of the trachea (shown in FIG. 19 (*i*)). In step 806, a needle of the device is inserted between the cartilage of the trachea (shown in FIG. 19 (*ii*)). In step 808, a plunger is depressed to extend a j-wire and to retract the needle (shown in FIG. 19 (iii)). In step 810, the device is advanced into the trachea such that wall members are positioned adjacent to the cartilage of the trachea. In step 812, the plunger is depressed to expand the wall members (shown in FIG. 19 (*iv*)). The wall members press against the patient's cartilaginous tracheal rings to dilate the patient's stoma. In step 814, the tracheostomy tube is slid off of the device and into the trachea. In step 816, the device is removed from the trachea (shown in FIG. 19 (*v*) and (vi)).

In some embodiments, step 808 can be preceded by a step of conducting a bubble test. A syringe partially loaded with a liquid can be inserted into the syringe port at the top of the plunger and drawn to confirm if the needle is in the patient's airway. If the needle is in the patient's airway, air passes from the tip of the needle through the lumens of the device and into the syringe. The presence of bubbles passing through the liquid in the syringe confirms the needle is in the patient's airway and not the surrounding tissue.

The method performs a percutaneous dilation tracheostomy procedure as in typical emergency tracheostomies, such as a Ciaglia Blue Rhino®. However, the improved percutaneous dilation tracheostomy device of the present invention allows an operator to perform the method steps of puncturing the patient with the needle, confirming proper puncture with a bubble test, retracting the needle, and dilating the patient's trachea. Thus, the method reduces the steps and time required to complete a percutaneous tracheotomy compared to a Seldinger technique and advantageously allows an operator to receive feedback from the device during the method. Furthermore, the dilation mechanism is configured to provide feedback from the dilation of the stoma, such as the feedback of a Laborde dilator as typically used in open surgical tracheostomies.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Prototype and Dilator Stress Test

Prototypes were manufactured using a 3D printer (e.g., MakerBot). The printer used an ABS plastic ink, although other inks or resins may be used, such as PLA and the like. Manufacturing the device with a 3D printer also included forming temporary supports, such as wax supports, within the device, such as in a hollow interior of the casing to support the components in a given position. Removing the temporary wax supports includes heating the casing and placing the casing in an ultrasonic tank.

Figure 20A:
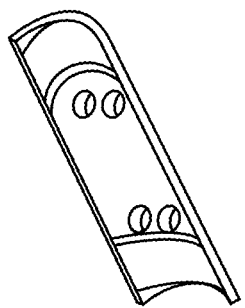
FIG. 20A though FIG. 20C depict the results of simulating stresses on the components of the dilator.
Figure 20B:
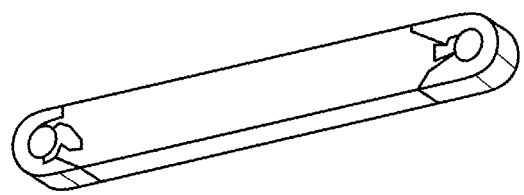
FIG. 20B depicts the deformation of the struts under an external pressure.
Figure 20C:
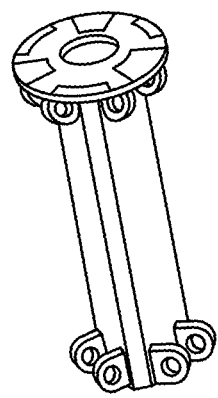
FIG. 20C depicts the deformation of the column under an external pressure.

A finite element analysis (FEA) was performed on the dilator wall members, struts, and central column to evaluate mechanical performance. The FEA constrained the wall members to zero degrees of freedom at the hinge pin connections and applied a pressure of 15 MPa to an exterior of the wall members to mimic the pressure of a tracheal wall upon dilation. The wall members were analyzed as having material properties of stainless steel. The FEA similarly constrained each of the struts and the central column and applied a pressure of 15 MPa to the interior of the hinge pin connections to simulate tracheal dilations. FIG. 20A illustrates one wall member stress values. FIG. 20B illustrates one strut stress values. FIG. 20C illustrates one central column stress values.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A percutaneous dilation tracheostomy device comprising:
 a hollow casing having an elongate cylindrical proximal section and a curved tubular distal section;
 a plunger mechanism housed within the casing;
 a dilating mechanism positioned in the curved tubular distal section, mechanically coupled to the plunger mechanism;
 a lumen running from a proximal end of the proximal section to a distal tip of the distal section; and
 a rotatable cam positioned within the proximal section of the casing distal to the plunger mechanism, the rotatable cam comprising a j-wire catch or a needle catch.

2. The device of claim 1, the rotatable cam comprising the j-wire catch.

3. The device of claim 2, comprising a flexible j-wire connected to the j-wire catch at a proximal end and extendable out of the distal tip.

4. The device of claim 1, the rotatable cam comprising the needle catch.

5. The device of claim 1, wherein the plunger mechanism comprises a depressible cylindrical plunger having a proximal end and a distal end positioned within the proximal section of the casing, the plunger comprising a portion of the lumen.

6. The device of claim 1, wherein the distal tip comprises a tapered outlet.

7. The device of claim 1, the dilating mechanism comprising a plurality of wall members positioned on an exterior surface of the curved tubular distal section.

8. The device of claim 1, further comprising an elongate flexible plunger connector positioned within the proximal section of the casing, extending into the distal section of the casing.

9. The device of claim 8, wherein the elongate flexible plunger connector comprises a portion of the lumen.

10. The device of claim 1, further comprising a side port positioned in the proximal section of the casing, the side port fluidly connected to an outlet of the distal tip.

11. The device of claim 1, wherein the distal section of the casing has an outer diameter between 5 mm and 25 mm.

12. The device of claim 1, wherein the dilating mechanism is configured to dilate a diameter of the curved tubular distal section by between 3 mm and 15 mm.

13. The device of claim 1, wherein the dilating mechanism is configured to support an applied pressure of at least 15 MPa when expanded.

14. A percutaneous dilation tracheostomy device comprising:
 a hollow casing having an elongate cylindrical proximal section and a curved tubular distal section;
 a plunger mechanism housed within the casing;
 a dilating mechanism positioned in the curved tubular distal section, mechanically coupled to the plunger mechanism, the dilating mechanism comprising a plurality of wall members positioned on an exterior surface of the curved tubular distal section; and
 a lumen running from a proximal end of the proximal section to a distal tip of the distal section, and
 wherein the plurality of wall members are configured to be expandable between a retracted configuration that positions each of the plurality of wall members flush against the exterior surface of the curved tubular distal section and an extended configuration that positions each of the plurality of wall members at an adjustable distance radially outward from the exterior surface of the curved tubular distal section.

15. The device of claim 14, wherein each of the plurality of wall members is radially equidistant from the lumen in the extended configuration.

16. The device of claim 14, the dilating mechanism further comprising a dilator column hingedly connected to a plurality of struts, each of the plurality of wall members being hingedly connected to two struts of the plurality of struts.

17. The device of claim 16, the plunger mechanism comprising a plunger depressible to advance the dilator column in a distal direction to move the plurality of wall members from the retracted configuration to the extended configuration.

18. A percutaneous dilation tracheostomy device comprising
 a hollow casing having an elongate cylindrical proximal section and a curved tubular distal section;
 a plunger mechanism housed within the casing;
 a dilating mechanism positioned in the curved tubular distal section, mechanically coupled to the plunger mechanism;
 a lumen running from a proximal end of the proximal section to a distal tip of the distal section; and
 a rotatable cam positioned within the proximal section of the casing distal to the plunger mechanism, and wherein the plunger mechanism comprises a plunger configured to rotate the cam.

* * * * *